United States Patent [19]

Schmitt-Willich et al.

[11] Patent Number: 5,820,849
[45] Date of Patent: Oct. 13, 1998

[54] CASCADE POLYMER COMPLEXES, PROCESS FOR THEIR PRODUCTION AND PHARAMCEUTICAL AGENTS CONTAINING SAID COMPLEXES

[75] Inventors: Heribert Schmitt-Willich; Johannes Platzek; Bernd Radüchel, all of Berlin; Andreas Mühler, Neuenhagen; Thomas Frenzel, Berlin, all of Germany

[73] Assignee: Schering Aktiengesellschaft, Berlin, Germany

[21] Appl. No.: 674,844

[22] Filed: Jul. 3, 1996

[30] Foreign Application Priority Data

Jul. 4, 1995 [DE] Germany ............ 195 25 924.6

[51] Int. Cl.⁶ ............ A61B 5/055; A61K 51/04; C07F 5/00
[52] U.S. Cl. .......... 424/9.36; 424/1.65; 424/9.361; 424/9.364; 424/9.365; 534/10; 534/14; 534/15; 534/16
[58] Field of Search ............ 424/1.65, 9.322, 424/9.34, 9.341, 9.36, 9.364, 9.365, 9.361; 534/10, 14, 15, 16; 540/465, 473, 474; 564/191, 198; 528/288, 328, 332, 310, 336

[56] References Cited

U.S. PATENT DOCUMENTS

| 4,587,329 | 5/1986  | Tomalia et al. ............ 528/363 |
| 4,863,717 | 9/1989  | Keana ............ 424/9 |
| 5,135,737 | 8/1992  | Keana ............ 424/9 |
| 5,281,704 | 1/1994  | Love et al. ............ 540/465 |
| 5,364,613 | 11/1994 | Sieving et al. ............ 424/9 |
| 5,364,614 | 11/1994 | Platzek et al. ............ 424/9 |
| 5,405,601 | 4/1995  | Dunn et al. ............ 424/9 |
| 5,446,145 | 8/1995  | Love et al. ............ 540/465 |
| 5,449,761 | 9/1995  | Belinka, Jr. et al. ............ 534/10 |
| 5,517,993 | 5/1996  | Unger et al. ............ 128/653.4 |
| 5,527,524 | 6/1996  | Tomalia et al. ............ 424/1.33 |
| 5,556,968 | 9/1996  | Carvalho et al. ............ 540/460 |
| 5,593,660 | 1/1997  | Krause et al. ............ 424/9.451 |

FOREIGN PATENT DOCUMENTS

| 2179624 | 6/1995  | Canada . |
| 2181070 | 9/1995  | Canada . |
| 2187921 | 11/1995 | Canada . |
| 2194560 | 1/1996  | Canada . |

OTHER PUBLICATIONS

"Dendrimer–based Metal Chelates: A New Class of Magnetic Resonance Imaging Contrast Agents," Magnetic Resonance in Medicine, 31(1):1–8, Jan. 1, 1994, Wiener et al.

Primary Examiner—Gary E. Hollinden
Assistant Examiner—Michael G. Hartley
Attorney, Agent, or Firm—Millen, White, Zelano & Branigan, P.C.

[57] ABSTRACT

Cascade polymer complexes that contain a) complexing ligands of general formula I $$A\text{-}\{X\text{-}[Y\text{-}(Z\text{-}<W\text{-}K_w>_z)_y]_x\}_a \qquad (I),$$

in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, K stands for the radical of a complexing agent, a stands for numbers 2 to 12, x, y, z and w, independently of one another, stand for numbers 1 to 4, provided that at least two reproduction units are different and that for the product of the multiplicities, $16 < a \cdot x \cdot y \cdot z \cdot w < 64$ holds true, b) at least 16 ions of an element of atomic numbers 20 to 29, 39, 42, 44 or 57–83, c) optionally cations of inorganic and/or organic bases, amino acids or amino acid amides as well as d) optionally acylated terminal amino groups are valuable compounds for diagnosis and therapy.

14 Claims, 1 Drawing Sheet

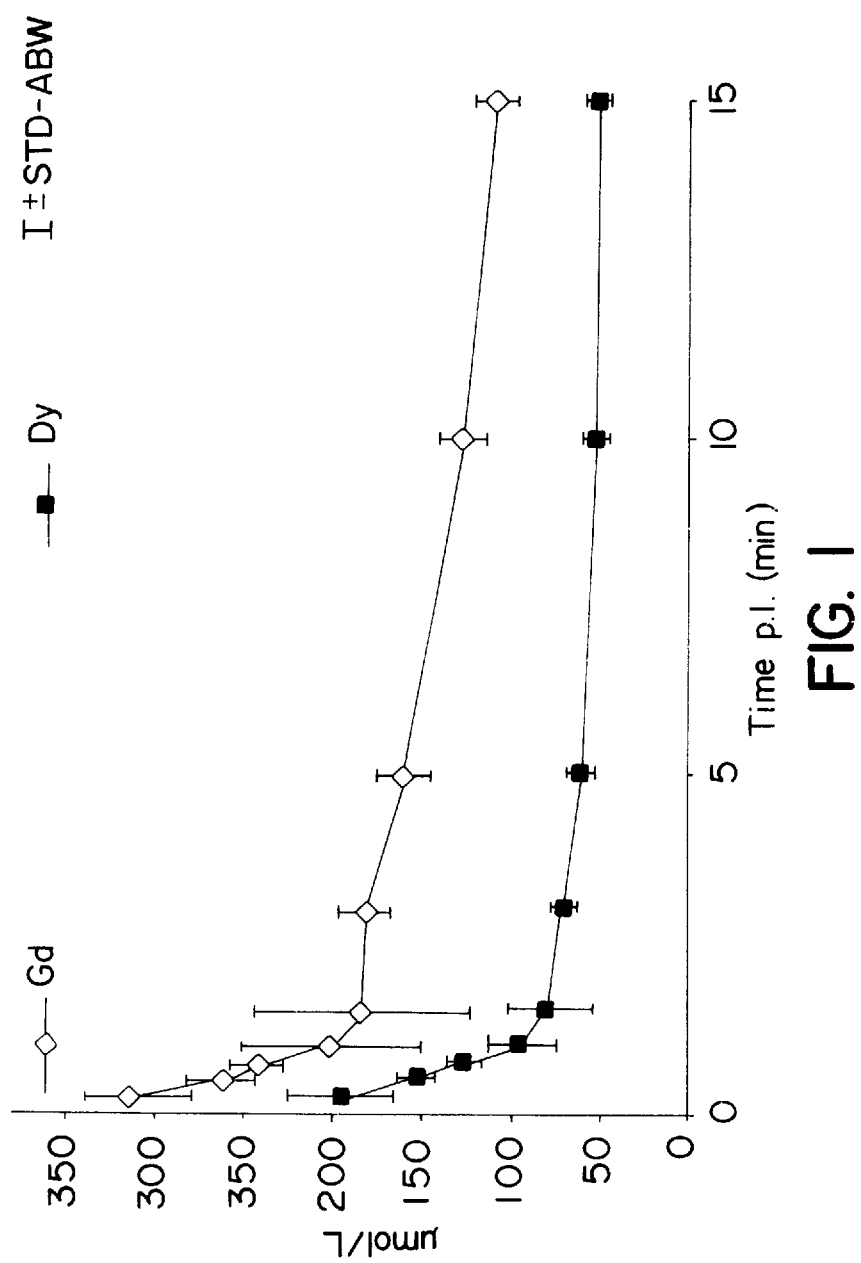

CASCADE POLYMER COMPLEXES, PROCESS FOR THEIR PRODUCTION AND PHARAMCEUTICAL AGENTS CONTAINING SAID COMPLEXES

The invention relates to new cascade polymer complexes, agents that contain these compounds, the use of the complexes in diagnosis and therapy, and a process for the production of these compounds and agents.

The contrast media that are now used in clinical practice for the modern imaging processes of nuclear spin tomography (MRI) and computer tomography (CT) [Magnevist®, Pro Hance®, Ultravist® and Omniscan®] are dispersed in the entire extracellular space of the body (intravascular space and interstitium). This dispersion space comprises about 20% of the volume of the body.

In clinical practice, extracellular MRI contrast media were first used successfully in the diagnosis of cerebral and spinal disease processes since here a quite special situation exists with respect to the regional dispersion space. In the brain and spinal cord, extracellular contrast media in healthy tissue do not leave the intravascular space because of the blood-brain barrier. In the case of pathological processes with disruption of the blood-brain barrier (e.g., malignant tumors, inflammations, demyelinating diseases, etc.), regions with elevated blood-vessel permeability then develop inside the brain for these extracellular contrast media (Schmiedl et al., MRI of Blood-Brain Barrier Permeability in Astrocytic Gliomas: Blood-Brain Barrier Permeability in Astrocytic Gliomas: Application of Small and Large Molecular Weight Contrast Media, Magn. Reson. Med. 22: 288, 1991). Affected tissue can be identified with high contrast relative to healthy tissue by exploiting this disruption of vascular permeability.

Outside of the brain and the spinal cord, however, no such permeability barrier exists for the above-mentioned contrast media (Canty et al., First-Pass Entry of Nonionic Contrast Agent into the Myocardial Extravascular Space. Effects on Radiographic Estimate of Transit Time and Blood Volume. Circulation 84: 2071, 1991). Thus, the concentration of the contrast medium is no longer dependent on vascular permeability, but only on the size of the extracellular space in the corresponding tissue. Delimitation of the vessels relative to the surrounding interstitial space using this contrast medium is not possible.

A contrast medium that is dispersed exclusively in the vascular space would be desirable, particularly for the visualization of vessels. The purpose of such a blood-pool agent is to make it possible, with the aid of nuclear spin tomography, to delimit tissue with sufficient blood supply from tissue with insufficient blood supply, and thus to diagnose an ischemia. Infarcted tissue can also be delimited, based on its anemia, from surrounding healthy or ischemic tissue if a vasal contrast medium is used. This is of special importance if, e.g., the point is to distinguish a myocardial infarction from an ischemia.

To date, most of the patients in whom there is suspicion of cardiovascular disease (this disease is the most frequent cause of death in Western industrialized countries) have to undergo invasive diagnostic tests. In angiography at present, diagnostic radiology with the aid of iodine-containing contrast media is used in particular. These tests suffer from various drawbacks: they are associated with the risk of radiation exposure, as well as with difficulties and stresses, which therefore particularly have the effect that the iodine-containing contrast media, as compared with NMR contrast media, have to be used in much higher concentrations.

There is therefore a need for NMR contrast media which can mark the vascular space (blood-pool agents). These compounds are to be distinguished by good compatibility and by high effectiveness (high increase of signal intensity with MRI).

Thus far, the attempt to solve at least a part of this problem by using complexing agents that are bound to macromolecules or biomolecules has been successful only to a limited extent.

Thus, for example, the number of paramagnetic centers in the complexes that are described in European Patent Applications No. 0 088 695 and No. 0 150 844 is not sufficient for satisfactory imaging.

If the number of metal ions required is increased by repeated introduction of complexing units into a macromolecular biomolecule, this is associated with an intolerable impairment of the affinity and/or specificity of this biomolecule [J. Nucl. Med. 24, 1158 (1983)].

Macromolecules can generally be suitable as contrast media for angiography. But 24 hours after intravenous injection in rats, albumin-GdDTPA (Radiology 1987; 162: 205), e.g., shows a concentration in the liver tissue that constitutes almost 30% of the dose. In addition, only 20% of the dose is eliminated in 24 hours.

The macromolecule polylysine-GdDTPA (European Patent Application, Publication No. 0 233 619) has also proved suitable as blood-pool agent. Because of production, however, this compound consists of a mixture of molecules of different sizes. In excretion tests in rats, it was shown that this macromolecule is excreted unchanged by glomerular filtration through the kidneys. Due to factors related to synthesis, however, polylysine-GdDTPA may also contain macromolecules that are so large that they cannot pass through the capillaries of the kidneys in the case of glomerular filtration and thus remain in the body.

Also, macromolecular contrast media based on carbohydrates, e.g., dextran, have been described (European Patent Application, Publication No. 0 326 226). The drawback of these compounds lies in the fact that the latter generally carry only about 5% of the signal-enhancing paramagnetic cation.

The polymers described in European Patent Application No. 0 430 863 already represent a step toward blood-pool agents since they no longer exhibit the size and molecular weight relative to heterogeneity that are characteristic of the previously mentioned polymers. They leave something to be desired, however, as regards complete elimination, compatibility, and/or effectiveness.

The object was therefore to make available new diagnostic tools particularly to identify and locate vascular diseases that do not have the above-mentioned drawbacks. This object is achieved by this invention.

It has been found that complexes which consist of nitrogen-containing cascade polymers that are provided with complexing ligands, at least 16 ions of an element of atomic numbers 20–29, 39, 42, 44 or 57–83, and optionally cations of inorganic and/or organic bases, amino acids or amino acid amides, and which optionally contain acylated amino groups are surprisingly very well suited for the production of NMR and x-ray diagnostic agents without exhibiting the mentioned drawbacks.

The complexing cascade polymers according to the invention can be described by general formula I

in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, K stands for the radical of a complexing agent, a stands for numbers 2 to 12, x, y, z and w, independently of one another, stand for numbers 1 to 4, provided that at least two reproduction units are different and that $$16 \leq a \cdot x \cdot y \cdot z \cdot w \leq 64$$

holds true for the product of the multiplicities. As cascade nucleus A, the following are suitable: nitrogen atom,

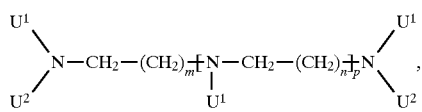

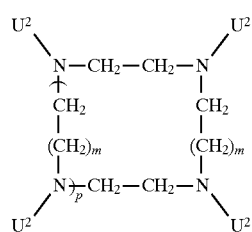

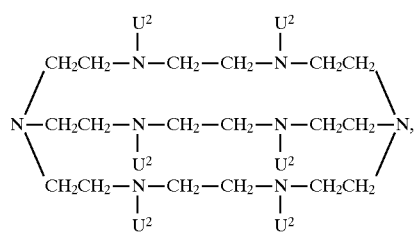

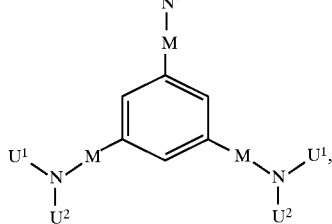

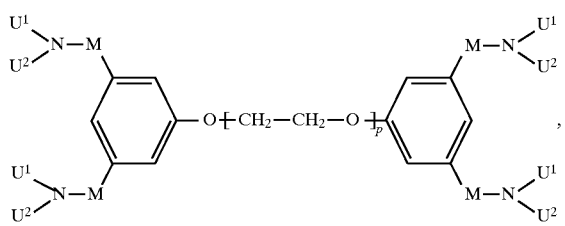

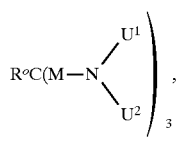

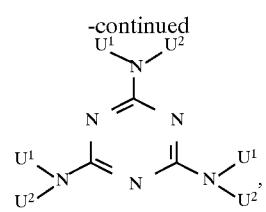

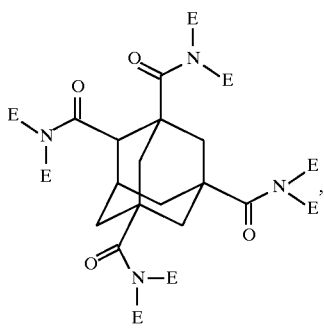

in which m and n stand for numbers 1 to 10, p stands for numbers 0 to 10, $U^1$ stands for $Q^1$ or E, $U^2$ stands for $Q^2$ or E with E meaning the group

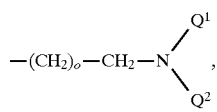

whereby o stands for numbers 1 to 6, $Q^1$ stands for a hydrogen atom or $Q^2$ and $Q^2$ stands for a direct bond, M stands for a $C_1$–$C_{10}$ alkylene chain which optionally is interrupted by 1 to 3 oxygen atoms and/or optionally is substituted with 1 to 2 oxo groups, $R^o$ stands for a branched or unbranched $C_1$–$C_{10}$ alkyl radical, a nitro, amino, carboxylic acid group or for

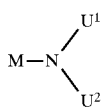

whereby the number of $Q^2$ elements corresponds to base multiplicity a.

The nitrogen atom, whose three bonds (base multiplicity a=3) in a first "inner layer" (generation 1) are occupied by three reproduction units X or Y (if X stands for a direct bond) or Z (if X and Y in each case stand for a direct bond), represents the simplest case of a cascade nucleus; in other words: the three hydrogen atoms of the basic cascade starter ammonia $A(H)_a = NH_3$ have been substituted by three reproduction units X or Y or Z. In this case, the number of $Q^2$ elements contained in cascade nucleus A represents base multiplicity a.

Reproduction units X, Y, Z and W contain —$NQ^1Q^2$ groups, in which $Q^1$ means a hydrogen atom or $Q^2$ and $Q^2$ means a direct bond. The number of $Q^2$ elements contained in the respective reproduction unit (e.g., X) corresponds to the reproduction multiplicity of this unit (e.g., x in the case of X). The product of all multiplicities a·x·y·z·w indicates the number of complexing agent radicals K bound in the cascade polymers. The polymers according to the invention contain at least 16 and at most 64 radicals K in the molecule, which in each case can bond one to a maximum of three (in the case of divalent ions), preferably one, ion of an element of the above-mentioned atomic numbers.

The last generation, i.e., reproduction unit W bound to complexing agent radical K, is bound to K with NH groups (—NQ$^1$Q$^2$ with Q$^1$ meaning a hydrogen atom and Q$^2$=direct bond), while the preceding reproduction units can be linked together both by NHQ$^2$ groups (e.g., by acylation reactions) and by NQ$^2$Q$^2$ groups (e.g., by alkylation reactions).

BRIEF DESCRIPTION OF THE DRAWINGS

FIG. 1 is a graph of the measured concentrations of Gd (compound 1) and Dy (compound 2) in rats (n=5) with ligated renal vessels, as described in the above Example for an In Vivo Comparison with an Extracellular Contrast Medium.

The cascade polymer complexes according to the invention exhibit a maximum of 10 generations (i.e., more than just one of reproduction units X, Y and Z can also be present in the molecule in each case), but preferably 2 to 4 generations, in which at least two of the reproduction units in the molecule are different.

As preferred cascade nuclei A, those are indicated which fall under the above-mentioned general formulas if
   m stands for numbers 1–3, especially preferably for number 1,
   n stands for numbers 1–3, especially preferably for number 1,
   o stands for number 1,
   M stands for a —CH$_2$, —CO or —CH$_2$CO group and
   R$^o$ stands for a —CH$_2$NU$^1$U$^2$, CH$_3$ or NO$_2$ group.

As further preferred cascade starters A(H)$_a$, there can be listed, e.g.:

(In the parentheses, base multiplicity a is indicated for the case where subsequent mono- or disubstitution is used in building the next generation)

| | |
|---|---|
| Tris(aminoethyl)amine | (a = 6 or 3); |
| tris(aminopropyl)amine | (a = 6 or 3); |
| diethylenetriamine | (a = 5 or 3); |
| triethylenetetramine | (a = 6 or 4); |
| tetraethylenepentamine | (a = 7 or 5); |
| 1,3,5-tris(aminomethyl)benzene | (a = 6 or 3); |
| trimesic acid triamide | (a = 6 or 3); |
| 1,4,7-triazacyclononane | (a = 3); |
| 1,4,7,10-tetraazacyclododecane | (a = 4); |
| 1,4,7,10,13-pentaazacyclopentadecane | (a = 5); |
| 1,4,8,11-tetraazacyclotetradecane | (a = 4); |
| 1,4,7,10,13,16-hexaazacyclooctadecane | (a = 6); |
| 1,4,7,10,13,16,19,22,25,28-decaazacyclotriacontane | (a = 10); |
| tetrakis(aminomethyl)methane | (a = 8 or 4); |
| 1,1,1-tris(aminomethyl)ethane | (a = 6 or 3); |
| tris(aminopropyl)-nitromethane | (a = 6 or 3); |
| 2,4,6-triamino-1,3,5-triazine | (a = 6 or 3); |
| 1,3,5,7-adamantanetetracarboxylic acid amide | (a = 8 or 4); |
| 3,3',5,5'-diphenylether-tetracarboxylic acid amide | (a = 8 or 4); |
| 1,2-bis[phenoxyethane]-3',3",5',5"-tetracarboxylic acid amide | (a = 8 or 4); |
| 1,4,7,10,13,16,21,24-octaazabicyclo[8.8.8]hexacosan | (a = 6). |

It can be pointed out that the definition as cascade nucleus A and thus the separation of cascade nucleus and first reproduction unit can be selected by purely formal means and thus independently of the actual synthesis of the desired cascade polymer complexes. Thus, e.g., the tris(aminoethyl) amine used in Example 4 can be considered as cascade nucleus A itself (compare the general formula, indicated first for A, with m=n=p=1, U$^1$=E with o meaning number 1 and U$^1$=U$^2$=Q$^2$) but also as a nitrogen atom (=cascade nucleus A), which as a first generation exhibits three reproduction units

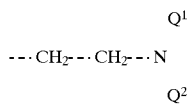

(compare the definition of E).

Suitable cascade reproduction units X, Y, Z and W are, independently of one another,

E,

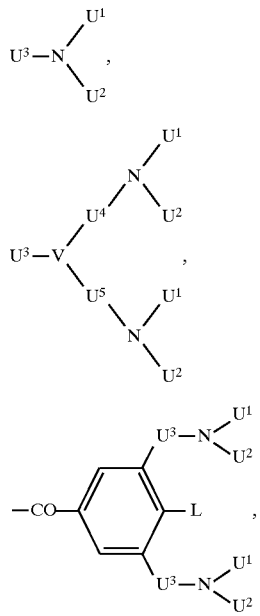

in which
   U$^1$ stands for Q$^1$ or E,
   U$^2$ stands for Q$^2$ or E with
   E meaning the group

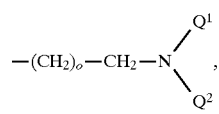

whereby
   o stands for numbers 1 to 6,
   Q$^1$ stands for a hydrogen atom or Q$^2$,
   Q$^2$ stands for a direct bond,
   U$^3$ stands for a C$_1$–C$_{20}$ alkylene chain, which optionally is interrupted by 1 to 10 oxygen atoms and/or 1 to 2—N(CO)$_q$—R$^2$ radicals, 1 to 2 phenylene radicals and/or 1 to 2 phenylenoxy radicals and/or optionally is substituted by 1 to 2 oxo, thioxo, carboxy, C$_1$–C$_5$ alkylcarboxy, C$_1$–C$_5$ alkoxy, hydroxy, C$_{1–C5}$ alkyl groups,
whereby
   q stands for numbers 0 or 1 and $R^2$ stands for a hydrogen atom, a methyl or an ethyl radical, which optionally is substituted with 1–2 hydroxy or 1 carboxy group(s), L stands for a hydrogen atom or the group

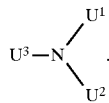

V stands for methine group

if at the same time $U^4$ means a direct bond or group M and $U^5$ has one of the meanings of $U^3$ or V stands for group

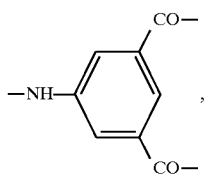

if at the same time $U^4$ and $U^5$ are identical and mean the direct bond or group M.

Preferred cascade reproduction units X, Y, Z and W are those in which in the above-mentioned general formulas, radical $U^3$ stands for —CO—, —COCH$_2$OCH$_2$CO—, —COCH$_2$—, —CH$_2$CH$_2$—, —CONHC$_6$H$_4$—, —COCH$_2$CH$_2$CO—, —COCH$_2$—CH$_2$CH$_2$CO—, —COCH$_2$CH$_2$CH$_2$CH$_2$CO—, radical $U^4$ stands for a direct bond, for —CH$_2$CO—, radical $U^5$ stands for a direct bond, for —(CH$_2$)$_4$—, —CH$_2$CO—, —CH(COOH)—, CH$_2$OCH$_2$CH$_2$—, —CH$_2$C$_6$H$_4$—, CH$_2$—C$_6$H$_4$OCH$_2$CH$_2$—, radical E stands for a group

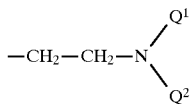

The following can be cited as examples of cascade reproduction units X, Y, Z and W:

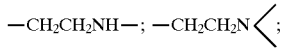

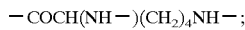

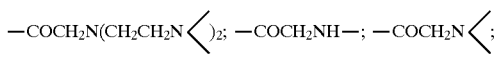

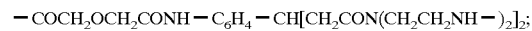

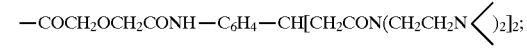

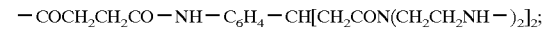

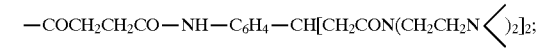

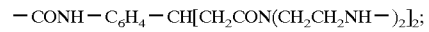

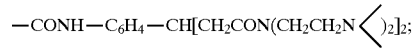

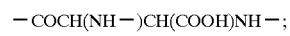

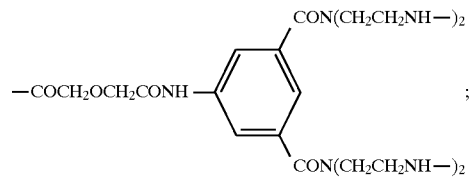

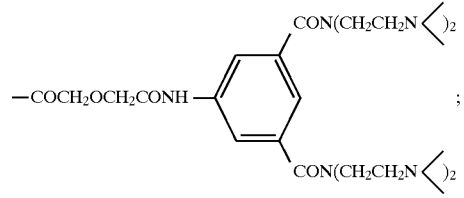

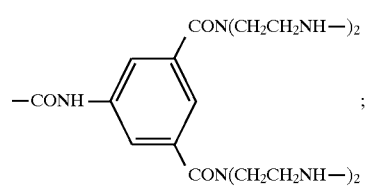

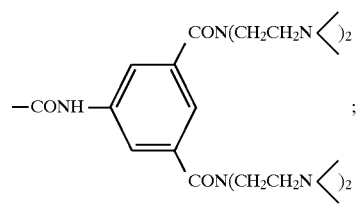

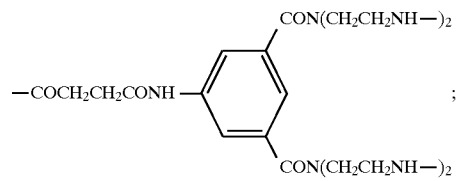

-continued

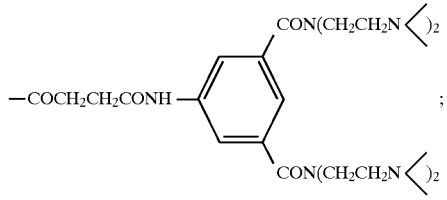

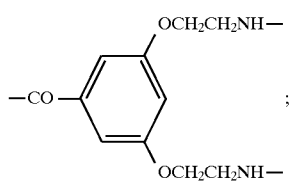

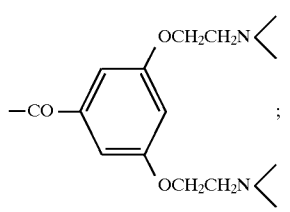

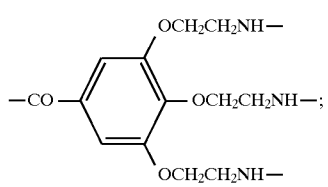

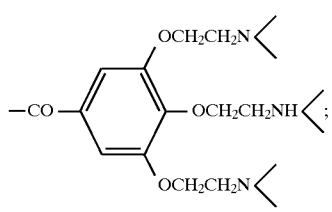

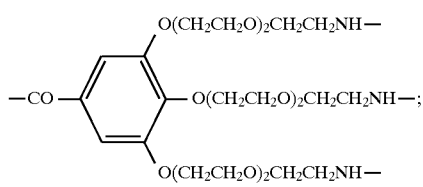

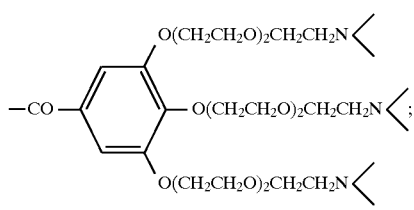

Complexing agent radicals K include those of general formulas IA and IB:

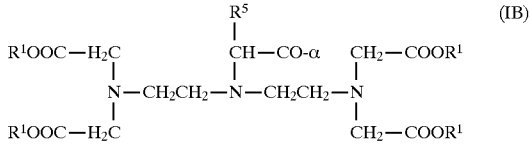

in which $R^1$, independently of one another, stand for a hydrogen atom or a metal ion equivalent of atomic numbers 20–29, 39, 42–44 or 57–83, $R^2$ stands for a hydrogen atom, a methyl or an ethyl radical which optionally is substituted with 1–2hydroxy or 1 carboxy group(s), $R^3$ stands for a

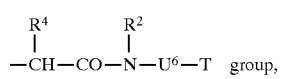

$R^4$ stands for a straight-chain, branched, saturated or unsaturated $C_1$–$C_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s), $R^5$ stands for a hydrogen atom or for $R^4$, $U^6$ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), whereby the phenylene groups that optionally can be contained can be substituted by 1–2 carboxy, 1–2 sulfo or 1–2 hydroxy groups, T stands for a —CO—α, —NHCO—α or —NHCS—α group, and α stands for the bonding site to the terminal nitrogen atoms of the last generation, of reproduction unit W.

As preferred complexing agent radicals K, those can be mentioned in which in above-indicated formula IA, the $C_1$–$C_{20}$, and preferably $C_1$–$C_{12}$ alkylene chain that stands for $U^6$ contains the groups —$CH_2$, —$CH_2NHCO$, —$NHCOCH_2O$, —$NHCOCH_2OC_6H_4$, —$N(CH_2CO_2H)$, —$NHCOCH_2C_6H_4$, —$NHCSNHC_6H_4$, —$CH_2OC_6H_4$, —$CH_2CH_2O$ and/or is substituted by groups —COOH, —$CH_2COOH$.

As examples for $U^6$, the following groups can be cited:

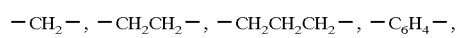

-continued

—C₆H₁₀—, —CH₂C₆H₅—,

—CH₂NHCOCH₂CH(CH₂CO₂H)—C₆H₄—,

—CH₂NHCOCH₂OCH₂—,

—CH₂NHCOCH₂C₆H₄—,

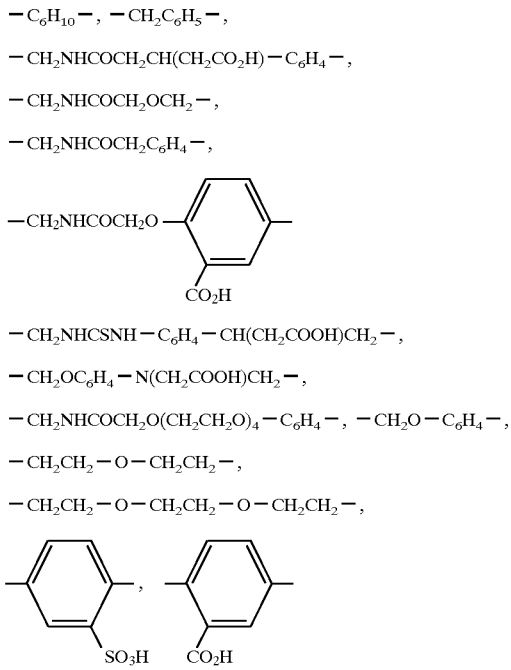

—CH₂NHCSNH—C₆H₄—CH(CH₂COOH)CH₂—,

—CH₂OC₆H₄—N(CH₂COOH)CH₂—,

—CH₂NHCOCH₂O(CH₂CH₂O)₄—C₆H₄—, —CH₂O—C₆H₄—,

—CH₂CH₂—O—CH₂CH₂—,

—CH₂CH₂—O—CH₂CH₂—O—CH₂CH₂—,

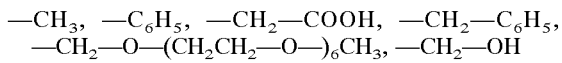

As examples for $R^4$, the following groups can be indicated:

—CH₃, —C₆H₅, —CH₂—COOH, —CH₂—C₆H₅, —CH₂—O—(CH₂CH₂—O—)₆CH₃, —CH₂—OH

If the agent according to the invention is intended for use in NMR diagnosis, the central ion of the complex salt must be paramagnetic. These are especially the divalent and trivalent ions of the elements of atomic numbers 21–29, 42, 44, and 58–70. Suitable ions are, for example, the chromium (III), iron(II), cobalt(II), nickel(II), copper(II), praseodymium(III), neodymium(III), samarium(III), and ytterbium(III) ions. Because of their very strong magnetic moment, the gadolinium(III), terbium(III), dysprosium(III), holmium(III), erbium(III), manganese(II), and iron(III) ions are especially preferred.

If the agent according to the invention is intended for use in diagnostic radiology, the central ion has to be derived from an element of higher atomic number in order to achieve sufficient absorption of the x rays. It has been found that for this purpose, diagnostic agents which contain a physiologically compatible complex salt with central ions of elements of atomic numbers between 21–29, 39, 42, 44, 57–83 are suitable; these are, for example, the lanthanum(III) ion and the above-mentioned ions of the lanthanide series.

The cascade polymer complexes according to the invention contain at least 16 ions of an element of the above-mentioned atomic numbers.

The remaining acid hydrogen atoms, i.e., those which were not substituted by the central ion, optionally can be replaced completely or partially by cations of inorganic and/or organic bases, amino acids, or amino acid amides.

Suitable inorganic cations are, for example, the lithium ion, the potassium ion, the calcium ion, the magnesium ion, and especially the sodium ion. Suitable cations of organic bases are, i.a., those of primary, secondary, or tertiary amines, such as, for example, ethanolamine, diethanolamine, morpholine, glucamine, N,N-dimethylglucamine, and especially N-methylglucamine. Suitable cations of amino acids are, for example, those of lysine, arginine, and ornithine, as well as the amides of otherwise acidic or neutral amino acids.

The compounds according to the invention, which have a molecular weight of 10,000–80,000 D, preferably 15,000–40,000 D, exhibit the desired properties described above. They contain the large number, required for their use, of metal ions bound in a stable manner in the complex.

They accumulate in regions with high vascular permeability, such as, e.g., in tumors, they make it possible to make observations regarding the perfusion of tissues, and they provide the possibility of determining the blood volume in tissues, of shortening selectively the relaxation times or densities of the blood, and of graphically representing the permeability of blood vessels. Such physiological data cannot be obtained through the use of extracellular contrast media, such as, e.g., Gd-DTPA [Magnevist®]. From these standpoints, there also follow the uses in the modern imaging processes of nuclear spin tomography and computer tomography: more specific diagnoses of malignant tumors, early therapy monitoring in cases where cytostatic, antiphlogistic, or vasodilative therapy is used, early identification of underperfused regions (e.g., in the myocardium), angiography in vascular diseases, and identification and diagnosis of (sterile or infectious) inflammations.

The cascade polymer complexes according to the invention are also extremely well suited for (interstitial and i.v.) lymphography.

As further advantages relative to extracellular contrast media, such as, e.g., Gd-DTPA [Magnevist®], the greater effectiveness as contrast media for nuclear spin tomography (higher relaxivity) must be emphasized; this ensures a marked reduction of the diagnostically required dose. At the same time, the contrast media according to the invention can be formulated as solutions in an isoosmolar manner in the blood and thus reduce the osmotic stress of the body, which is reflected in a reduced toxicity on the part of the substance (higher toxic threshold). Smaller doses and higher toxic thresholds result in a significant increase of the reliability of contrast medium use in modern imaging processes.

In comparison with macromolecular contrast media based on carbohydrates, e.g., dextran (European Patent Application, Publication No. 0 326 226), which carry—as mentioned—generally only about 5% of the signal-enhancing paramagnetic cation, the polymer complexes according to the invention exhibit a content of the paramagnetic cation of generally about 20%, although this figure is not intended to be necessarily limiting. Thus, the macromolecules according to the invention produce much better signal enhancement per molecule, which simultaneously has the effect that the dose necessary for nuclear spin tomography is considerably smaller relative to macromolecular contrast media based on carbohydrates.

With the polymer complexes according to the invention, it has been possible to design and produce macromolecules in such a way that the latter have a uniformly defined molecular weight. It is thus possible, surprisingly enough, to control the size of the macromolecules in such a way that the latter are large enough to be able to leave the vascular space only slowly, but at the same time small enough to be able to pass through the capillaries of the kidneys, which are 300–800 Å in size.

In comparison to the other mentioned polymer compounds of the prior art, the cascade polymer complexes according to the invention are distinguished by improved excretion behavior, greater effectiveness, greater stability, and/or better compatibility.

Another advantage of this invention lies in the fact that now complexes with hydrophilic or lipophilic, macrocyclic or open-chain, low-molecular weight, or high-molecular weight ligands have become accessible. As a result, the possibility exists for controlling the compatibility and pharmacokinetics of these polymer complexes by chemical substitution.

The production of the cascade polymer complexes according to the invention takes place in that compounds of general formula I'

  (I'), in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, a stands for numbers 2 to 12, x, y, z and w, independently of one another, stand for numbers 1 to 4 and β stands for the bonding site of the terminal NH groups of the last generation, of reproduction unit W provided that at least two reproduction units are different, and that for the product of multiplicities, $16 \leq a \cdot x \cdot y \cdot z \cdot w \leq 64$, $16 \leq a \cdot x \cdot y \cdot z \cdot w \leq 64$, holds true, are reacted with a complex or complexing agent K' of general formula I'A or I'B

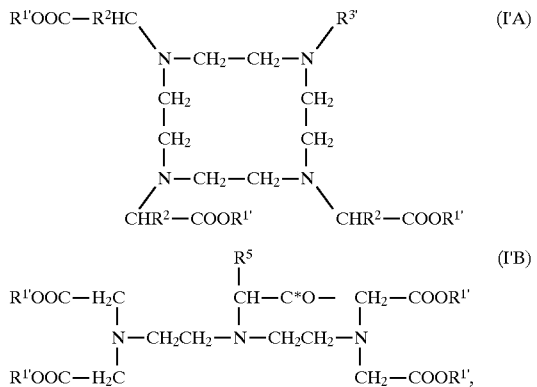

whereby $R^{1'}$, independently of one another, stand for a hydrogen atom, a metal ion equivalent of atomic numbers 20–29, 39, 42–44, or 57–83 or an acid protective group, $R^2$ stands for a hydrogen atom, a methyl or an ethyl radical which optionally is substituted with 1–2 hydroxy or 1 carboxy group(s), $R^{3'}$ stands for a

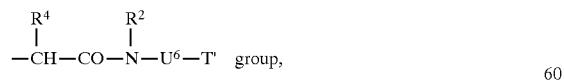

$R^4$ stands for a straight-chain, branched, saturated or unsaturated $C_1$–$C_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s), $R^5$ stands for a hydrogen atom or for $R^4$, $U^6$ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), whereby the phenylene groups that are optionally contained can be substituted by 1–2 carboxy, 1–2 sulfo or 1–2 hydroxy groups, T' stands for a —C*O, —COOH, —N=C=O or —N=C=S group, and C*O stands for an activated carboxyl group, provided that—if K' stands for a complex—at least two (in the case of divalent metals) or three (in the case of trivalent metals) of substituents $R^1$ stand for a metal ion equivalent of the above-mentioned elements and that optionally other carboxyl groups are present in the form of their salts with inorganic and/or organic bases, amino acids or amino acid amides, are reacted, optionally present protective groups are cleaved, the thus obtained cascade polymers—if K' stands for a complexing agent—are reacted in a way known in the art with at least one metal oxide or metal salt of an element of atomic numbers 20–29, 39, 42, 44, or 57–83 and then optionally in the cascade polymer complexes thus obtained, acid hydrogen atoms that are still present are completely or partially substituted by cations of inorganic and/or organic bases, amino acids, or amino acid amides, and optionally still present free terminal amino groups are optionally acylated—before or after the metal complexing.

Another aspect of this invention is represented by the new compounds of general formula I'A

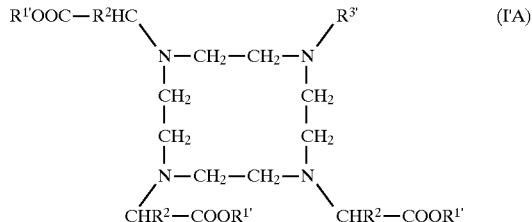

whereby $R^{1'}$, independently of one another, stand for a hydrogen atom, a metal ion equivalent of atomic numbers 20–29, 39, 42–44 or 57–83 or an acid protective group, $R^2$ stands for a hydrogen atom, a methyl or an ethyl radical, which optionally is substituted with 1–2 hydroxy or 1 carboxy group(s), $R^{3'}$ stands for a

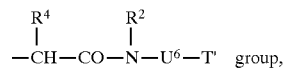

$R^4$ stands for a straight-chain, branched, saturated or unsaturated $C_1$–$C_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s), $U^6$ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), whereby the phenylene groups that are optionally contained can be substituted by 1–2 carboxy, 1–2 sulfo or 1–2 hydroxy groups, T' stands for a —C*O, —COOH, —N=C=O or —N=C=S group, and C*O stands for an activated carboxyl group.

They are used as important intermediate products for the production of the cascade polymer complexes of general formula I.

As an example of an activated carbonyl group C*O in complexes or complexing agents K', anhydride, p-nitrophenyl ester, N-hydroxysuccinimide ester, pentafluorophenyl ester, and acid chloride can be mentioned.

The addition or acylation that is carried out to introduce the complexing agent units is performed with substrates that contain desired substituents K (optionally bound to a leaving group) or from which the desired substituent is generated by the reaction.

As examples of addition reactions, the reaction of isocyanates and isothiocyanates can be mentioned, whereby the reaction of isocyanates is preferably performed in aprotic solvents, such as, e.g., THF, dioxane, DMF, DMSO, methylene chloride at temperatures of between 0° and 100° C., preferably between 0° and 50° C., optionally with the addition of an organic base such as triethylamine, pyridine, lutidine, N-ethyldiisopropylamine, N-methylmorpholine. The reaction with isothiocyanates is generally performed in solvents, such as, e.g., water or lower alcohols, such as, e.g., methanol, ethanol, isopropanol or their mixtures, DMF or mixtures of DMF and water at temperatures of between 0° and 100° C., preferably between 0° and 50° C., optionally with the addition of an organic or inorganic base, such as, e.g., triethylamine, pyridine, lutidine, N-ethyldiisopropylamine, N-methylmorpholine, or alkaline-earth hydroxides, alkali hydroxides, such as, e.g., lithium, sodium, potassium, calcium hydroxide, or their carbonates, such as, e.g., magnesium carbonate.

As examples of acylation reactions, the reaction of free carboxylic acids according to the methods known to one skilled in the art [e.g., J. P. Greenstein, M. Winitz, Chemistry of the Amino Acids, John Wiley & Sons, N.Y. (1961), pp. 943–945] can be mentioned. It has proven advantageous, however, to convert the carboxylic acid group before the acylation reaction to an activated form, such as, e.g., anhydride, active ester or acid chloride [e.g., E. Gross, J. Meienhofer, The Peptides, Academic Press, N.Y. (1979), Vol. 1, pp. 65–314; N. F. Albertson, Org. React. 12, 157 (1962)].

In the case of reaction with active ester, the literature known to one skilled in the art [e.g., Houben-Weyl, Methoden der organischen Chemie [Methods of Organic Chemistry], Georg Thieme Verlag, Stuttgart, Volume E 5 (1985), 633] can be cited. This reaction can be performed under the conditions indicated above for the anhydride reaction. However, aprotic solvents, such as, e.g., methylene chloride, chloroform, can also be used.

In the case of acid chloride reactions, only aprotic solvents, such as, e.g., methylene chloride, chloroform, toluene or THF, at temperatures between −20° to 50° C., preferably between 0° to 30° C., are used. Further, literature known to one skilled in the art [e.g., Houben-Weyl, Methoden der Organischen Chemie, Georg-Thieme-Verlag, Stuttgart, (1974), Volume 15/2, pp. 355–364) can be cited.

If $R^{1'}$ stands for an acid protective group, lower alkyl, aryl and aralkyl groups, for example, the methyl, ethyl, propyl, butyl, phenyl, benzyl, diphenylmethyl, triphenylmethyl, bis-(p-nitrophenyl)-methyl groups, as well as trialkylsilyl groups, are suitable.

The optionally desired cleavage of the protective groups takes place according to the processes known to one skilled in the art, for example by hydrolysis, hydrogenolysis, alkaline saponification of esters with alkali in aqueous-alcoholic solution at temperatures of 0° C. to 50° C. or in the case of tert-butyl esters with the aid of trifluoroacetic acid.

Terminal amino groups that are optionally incompletely acylated with ligands or complexes can optionally be converted to amides or semiamides. The reactions with acetic anhydride, succinic anhydride or diglycolic anhydride can be mentioned as examples.

The introduction of the desired metal ions takes place in the way in which it was disclosed, e.g., in German laid-open specification 34 01 052, by the metal oxide or a metal salt (for example, the nitrate, acetate, carbonate, chloride or sulfate) of the element of atomic numbers 20–29, 42, 44, 57–83 being dissolved or suspended in water and/or a lower alcohol (such as methanol, ethanol or isopropanol) and being reacted with the solution or suspension of the equivalent amount of complexing ligand and then optionally existing acid hydrogen atoms of the acid groups being substituted by cations of inorganic and/or organic bases, amino acids or amino acid amides.

The introduction of the desired metal ions can take place both in the stage of complexing agent I'A or I'B, i.e., before the coupling to the cascade polymers, and after coupling of unmetalated ligands I'A, I'B or I'C.

In this case, the neutralization takes place with the aid of inorganic bases (for example, hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methyl and N,N-dimethylglucamine, as well as basic amino acids, such as, for example, lysine, arginine and ornithine or of amides of originally neutral or acid amino acids, such as, for example, hippuric acid, glycine acetamide.

For the production of neutral complex compounds, enough of the desired bases can be added, for example, to the acid complex salts in aqueous solution or suspension that the neutral point is reached. The obtained solution can then be evaporated to dryness in a vacuum. Often, it is advantageous to precipitate the formed neutral salts by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others) and thus to obtain easily isolated and readily purified crystallizates. It has proven especially advantageous to add the desired bases as early as during the complexing of the reaction mixture and thus to save a process step.

If the acid complex compounds contain several free acid groups, it is often suitable to produce neutral mixed salts, which contain both inorganic and organic cations as counterions.

This can happen, for example, by the complexing ligands in aqueous suspension or solution being reacted with the oxide or salt of the element yielding the central ion and half of the amount of an organic base required for neutralization, the formed complex salt being isolated, optionally purified and then mixed with the required amount of inorganic base for complete neutralization. The sequence of the addition of base can also be reversed.

The purification of the thus obtained cascade polymer complexes takes place, optionally after adjusting the pH to 6 to 8, preferably about 7, by adding an acid or base, preferably by ultrafiltration with membranes of suitable pore size (e.g., Amicon®XM30, Amicon®YM10, Amicon®YM3) or gel filtration on, e.g., suitable Sephadex® gels.

In the case of neutral complex compounds, it is often advantageous to provide the polymeric complexes with an anion exchanger, for example, IRA 67 (OH⁻ form) and optionally in addition with a cation exchanger, for example, IRC 50 (H⁺ form) for the separation of ionic components.

The production of the cascade polymers carrying terminal amino groups required for the coupling to complexing agents K' (or else the corresponding metal-containing complexes) generally proceeds from nitrogen-containing cascade starters $A(H)_a$ that can be produced by commercially available methods or according to or analogously to methods known in the literature. The introduction of generations X, Y, Z and W takes place according to methods known in the literature [e.g., J. March, Advanced Organic Chemistry, 3rd ed.; John Wiley & Sons, (1985), 364–381] by acylation or alkylation reactions with protected amines exhibiting the desired structures, which contain functional groups capable of bonding to the cascade nuclei, such as, e.g., carboxylic acids, isocyanates, isothiocyanates or activated carboxylic acids (such as, e.g., anhydrides, active esters, acid chlorides) or halides (such as, e.g., chlorides, bromides, iodides), aziridine, mesylates, tosylates or other leaving groups known to one skilled in the art.

It can be stressed, however, that the differentiation between cascade nucleus A and reproduction units is purely formal. It can be advantageous synthetically that formal cascade starter $A(H)_a$ is not used, but rather the nitrogen atoms forming part of the cascade nucleus by definition are introduced first together with the first generation. Thus, e.g., for synthesis of the compound described in Example 1b), it is more advantageous not to alkylate the formal cascade nucleus trimesic acid triamide with e.g., benzyloxycarbonylaziridine (six-fold), but rather to react trimesic acid trichloride with bis[2-(benzyloxycarbonylamino)-ethyl]-amine (three-fold).

As amino protective groups, the benzyloxycarbonyl, tert-butoxycarbonyl, trifluoroacetyl, fluorenylmethoxycarbonyl, benzyl and formyl groups familiar to one skilled in the art [Th. W. Greene, P. G. M. Wuts, Protective Groups in Organic Syntheses, 2nd ed, John Wiley and Sons (1991), pp. 309–385] can be mentioned. After cleavage of these protective groups, which also takes place according to methods known in the literature, the next desired generation can be introduced into the molecule. In addition to this synthesis of a generation consisting of two reaction stages in each case (alkylation or acylation and protective group cleavage), the simultaneous introduction of two, e.g., $X-[Y]_x$, or several generations, e.g., $X-[Y-(Z)_y]_x$, is also possible with only two reaction stages. The synthesis of these multi-generation units takes place by alkylation or acylation of unprotected amines ("reproduction amine"), exhibiting the structures of the desired reproduction units, with a second reproduction amine, whose amine groups are present in protected form.

The compounds of general formula $A(H)_a$ required as cascade starters are commercially available or can be produced according to or analogously to methods known in the literature [e.g., Houben-Weyl, Methoden der Org. Chemie, Georg-Thieme-Verlag, Stuttgart (1957), Vol. 11/1; M. Micheloni et al., Inorg. Chem. (1985), 24, 3702; T. J. Atkins et al., Org. Synth., Vol. 58 (1978), 86–98; The Chemistry of Heterocyclic Compounds: J. S. Bradshaw et al., Aza-Crown-Macrocycles, John Wiley & Sons, N.Y. (1993)]. As examples, there can be cited:

Tris(aminoethyl)amine [e.g., Fluka Chemie [Fluka Chemistry] AG, Switzerland; Aldrich-Chemie [Aldrich Chemistry], Germany];

tris(aminopropyl)amine [e.g., C. Woerner et al., Angew. Chem. [Applied Chem.] Int. Ed. Engl. (1993), 32, 1306];

diethylenetriamine [e.g., Fluka; Aldrich];

triethylenetetramine [e.g., Fluka; Aldrich];

tetraethylenepentamine [e.g., Fluka; Aldrich];

1,3,5-tris(aminomethyl)benzene [e.g., T. M. Garrett et al., J. Am. Chem. Soc. (1991), 113, 2965];

trimesic acid triamide [e.g., H. Kurihara; Jpn. Kokai Tokyo Koho JP 04077481; CA 117, 162453];

1,4,7-triazacyclononane [e.g., Fluka; Aldrich];

1,4,7,10,13-pentaazacyclopentadecane [e.g., K. W. Aston, Eur. Pat. Appl. 0 524 161, CA 120, 44580];

1,4,7,10-tetraazacyclododecane [e.g., Aldrich] 1,4,8,11-tetraazacyclotetradecane [e.g., Fluka; Aldrich];

1,4,7,10,13,16,19,22,25,28-decaazacyclotriacontane [e.g., A. Andres et al., J. Chem. Soc. Dalton Trans. (1993), 3507];

1,1,1-tris(aminomethyl)ethane [e.g., R. J. Geue et al., Aust. J. Chem. (1983), 36, 927];

tris(aminopropyl)-nitromethane [e.g., G. R. Newkome et al., Angew. Chem. 103, 1205 (1991) analogously to R. C. Larock, Comprehensive Organic Transformations, VCH Publishers, N.Y. (1989), 419–420]

1,3,5,7-adamantanetetracarboxylic acid amide [e.g., H. Stetter et al., Tetr. Lett. 1967, 1841];

1,2-bis[phenoxyethane]-3',3",5',5"-tetracarboxylic acid amide [e.g., J. P. Collman et al.; J. Am. Chem. Soc. (1988), 110, 3477–86 analogously to the instructions for Example 1b)];

1,4,7,10,13,16,21,24-octaazabicyclo[8.8.8]hexacosane [e.g., P. H. Smith et al., J. Org. Chem. (1993), 58, 7939].

The production of the reproduction amines that contain the above-mentioned functional groups required for the synthesis of generations takes place according to or analogously to the instructions described in the experimental part or according to processes known in the literature.

As examples, there can be mentioned:

$N^\alpha,N^\epsilon$-Di-benzyloxycarbonyl-lysine-p-nitrophenyl ester [see instructions for Example 1c)];

HOOC—CH₂OCH₂CO—N(CH₂CH₂NH—CO—O—CH₂C₆H₅)₂;

HOOC—CH₂N(CH₂CH₂NH—CO—O—CH₂C₆H₅)₂;

HOOC—CH₂CH₂CO—N(CH₂CH₂NH—COCF₃)₂ [to be produced according to instructions for Example 3a), by starting from bis(trifluoroacetylaminoethyl)amine instead of bis(benzyloxyarbonylaminoethyl)amine and from succinic anhydride instead of diglycolic anhydride];

HOOC—CH₂OCH₂CONH—C₆H₄—CH[CH₂CON(CH₂CH₂NH—CO—O—CH₂C₆H₅)₂]₂ [to be produced analogously to instructions for Example 3a];

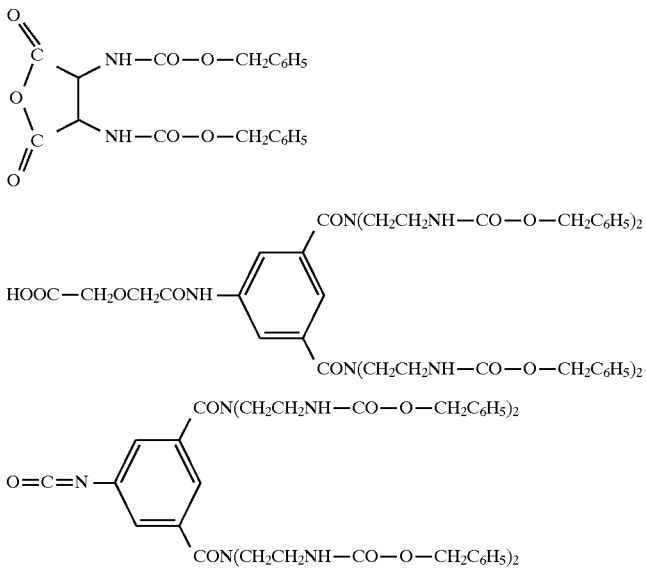

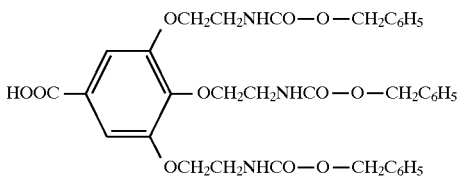

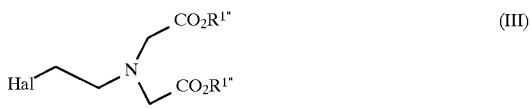

N-benzyloxycarbonyl-aziridine to be produced according to M. Zinic et al., J. Chem. Soc, Perkin Trans 1, 21–26 (1993) N-benzyloxycarbonyl-glycine commercially available in, e.g., Bachem, Calif.

to be produced according to C. J. Cavallito et al., J. Amer. Chem. Soc. 1943, 65, 2140, by starting from N—CO—O—$CH_2C_6H_5$—(2-bromoethyl)amine instead of benzyl chloride [A. R. Jacobson et al., J. Med. Chem. (1991), 34, 2816].

The production of the complexes and complexing agents of general formula I'A and I'B takes place according to or analogously to the instructions described in the experimental part or according to methods known in the literature (see, e.g., European Patent Applications Nos. 0 512 661, 0 430 863, 0 255 471 and 0 565 930).

Thus, the production of compounds of general formula I'A is carried out, e.g., in that a group T''' is used as a precursor of functional group T', either in the meaning of a protected acid function, which can be converted to the free acid function independently of acid protective groups $R^{1'}$ according to the above-indicated process, or in the meaning of a protected amine function, which unblocks according to processes known in the literature [Th. W. Greene, P. G. M. Wuts, Protective Groups in Organic Synthesis, 2nd edition, John Wiley & Sons (1991), pp. 309–385] and then can be converted to the isocyanates or isothiocyanates [Methoden der Org. Chemie (Houben-Weyl), E 4, pp. 742–749, 837–843, Georg Thieme Verlag, Stuttgart, New York (1983)]. Such compounds can be produced according to or analogously to the instructions that are described in the experimental part by monoalkylation of cyclene with suitable α-halogenated acid amides [in aprotic solvents, such as, e.g., chloroform].

The production of compounds of general formula I'B can be carried out, for example, in that a protected acid function is used as a precursor of the activated carboxyl group-C*O, which can be converted to the free acid function independently of acid protective groups $R^{1'}$ according to the above-indicated processes and can be activated according to the processes that are known in the literature and are also described above. Such compounds can be produced according to or analogously to the instructions that are described in the experimental part or, for example, in that an amino acid derivative of general formula II $$\underset{H_2N \quad CO_2V^1}{\overset{R^{5'}}{\wedge}} \qquad (II)$$

in which p1 $R^{5'}$ has the meaning indicated for $R^5$, whereby hydroxy or carboxy groups that are optionally contained in $R^5$ are optionally present in protected form, and $V^1$ is a straight-chain or branched $C^1$–$C_6$ alkyl group, a benzyl, trimethylsilyl, triisopropylsilyl, 2,2,2-trifluoroethoxy or 2,2,2-trichloroethoxy group, whereby $V^1$ is different from $R^{1''}$, is reacted with an alkylating agent of general formula III $$\text{(III)}$$

in which
$R^{1''}$ stands for a protective group, and
Hal stands for a halogen atom, such as Cl, Br or I, but preferably Cl [see also M. A. Williams, H. Rapoport, J. Org. Chem. 58, 1151 (1993)].

Preferred amino acid derivatives are the esters of naturally occurring α-amino acids.

The reaction of compound (II) with compound (III) is carried out preferably in a buffered alkylation reaction, whereby an aqueous phosphate-buffer solution is used as buffer. The reaction is carried out at pH 7–9, but preferably at pH 8. The buffer concentration can be between 0.1–2.5M, but preferably a 2M phosphate-buffer solution is used. The temperature of the alkylation can be between 0° and 50° C.; the preferred temperature is room temperature.

The reaction is carried out in a polar solvent, such as, e.g., acetonitrile, tetrahydrofuran, 1,4-dioxane or 1,2-dimethoxyethane. Preferably, acetonitrile is used.

The production of the pharmaceutical agents according to the invention takes place also in a way known in the art, by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriaminepentaacetic acid or the corresponding Ca-cascade polymer complexes) or—if necessary—electrolytes, such as, for example, sodium chloride or—if necessary—antioxidants, such as, for example, ascorbic acid.

If suspensions or solutions of the agents according to the invention in water or physiological salt solution are desired for enteral administration or other purposes, they are mixed with one or more adjuvant(s) that are commonly used in galenicals [for example, methylcellulose, lactose, mannitol] and/or surfactant(s) [for example, lecithins, Tween®, Myrj®] and/or flavoring substance(s) for taste correction [for example, ethereal oils].

In principle, it is also possible to produce the pharmaceutical agents according to the invention even without isolating the complex salts. In any case, special care must be used to undertake the chelation so that the salts and salt solutions according to the invention are practically free of noncomplexed metal ions having a toxic effect.

This can be assured, for example, with the aid of color indicators such as xylenol orange by control titrations during the production process. The invention therefore also relates to processes for the production of complex compounds and their salts. As a last precaution, there is a purification of the isolated complex salt.

The pharmaceutical agents according to the invention contain preferably 1 $\mu$mol–1.3 mol/l of the complex salt and are generally dosed in amounts of 0.0001–5 mmol/kg. They are intended for enteral and parenteral administration. The complex compounds according to the invention are used 1. for NMR diagnosis and diagnostic radiology in the form of their complexes with the ions of elements with atomic numbers 21–29, 39, 42, 44 and 57–83;
2. for radiodiagnosis and radiotherapy in the form of their complexes with radioisotopes of the elements with atomic numbers 27, 29, 31, 32, 37–39, 43, 49, 62, 64, 70, 75 and 77.

The agents according to the invention meet the varied requirements for suitability as contrast media for nuclear spin tomography. Thus, they are very well suited, after oral or parenteral administration, for improving the image, obtained with the aid of nuclear spin tomographs, in its informative value by increasing the signal intensity. Further, they show the great effectiveness which is necessary to load the body with the fewest possible amounts of foreign substances, and the good compatibility which is necessary to maintain the noninvasive nature of the studies.

The good water solubility and low osmolality of the agents according to the invention makes it possible to produce highly concentrated solutions, so that the volume load of the circulatory system can be held within reasonable limits, and to compare the dilution through the bodily fluid, i.e., NMR diagnostic agents must be 100- to 1000-fold more water-soluble than for NMR spectroscopy. Further, the agents according to the invention exhibit not only a high stability in vitro, but also a surprisingly high stability in vivo, so that a release or an exchange of the ions—toxic in themselves—not covalently bound in the complexes, in which the new contrast media are again completely excreted, takes place only extremely slowly.

In general, the agents according to the invention for use as NMR diagnostic agents are dosed in amounts of 0.001–5 mmol/kg, preferably 0.005–0.5 mmol/kg. Details of use are discussed, for example, in H. -J. Weinmann et al., Am. J. of Roentgenology 142, 619 (1984).

Especially low dosages (under 1 mg/kg of body weight) of organ-specific NMR diagnostic agents can be used, for example, to detect tumors and myocardial infarction.

Further, the complex compounds according to the invention are used advantageously as susceptibility reagents and as shift reagents for in vivo NMR spectroscopy.

The agents according to the invention are also suitable as radiodiagnostic agents because of their advantageous radioactive properties and the good stability of the complex compounds contained in them. Details of their use and dosage are described, e.g., in "Radiotracers for Medical Applications," CRC Press, Boca Raton, Fla.

Another imaging method with radioisotopes is positron emission tomography, which uses positron-emitting isotopes, such as, e.g., $^{43}$Sc, $^{44}$Sc, $^{52}$Fe, $^{55}$Co and $^{68}$Ga (Heiss, W. D.; Phelps, M. E.; Positron Emission Tomography of the Brain, Springer Verlag Berlin, Heidelberg, New York 1983).

The compounds according to the invention are also suitable, surprisingly enough, for differentiating malignant and benign tumors in areas without blood-brain barriers.

They are also distinguished in that they are eliminated completely from the body and thus are well compatible.

Since the substances according to the invention are concentrated in malignant tumors (no diffusion in healthy tissue, but high permeability of tumor vessels), they can also assist in the radiation therapy of malignant tumors. The latter is distinguished from the corresponding diagnosis only by the amount and type of the isotope used. The object, in this case, is the destruction of tumor cells by high-energy shortwave radiation with a smallest possible range of action. For this purpose, interactions of the metals contained in the complexes (such as, e.g., iron or gadolinium) are used with ionizing radiations (e.g., x rays) or with neutron rays. By this effect, the local radiation dose is significantly increased on the spot where the metal complex is found (e.g., in tumors). To produce the same radiation dose in the malignant tissue, the radiation exposure for healthy tissue can be considerably reduced with the use of such metal complexes and thus side effects that are stressful to the patients are avoided. The metal complex conjugates according to the invention are therefore suitable also as radiosensitizing substances in radiation therapy of malignant tumors (e.g., use of Mössbauer effects or in neutron capture therapy). Suitable $\beta$-emitting ions are, for example, $^{46}$Sc, $^{47}$Sc, $^{48}$Sc, $^{72}$Ga, $^{73}$Ga and $^{90}$Y. Suitable $\alpha$-emitting ions exhibiting small half-lives are, for example, $^{211}$Bi, $^{212}$Bi, $^{213}$Bi and $^{214}$Bi, and $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy proposed by R. L. Mills et al. (Nature Vol. 336, (1988), p. 787), the central ion must be derived from a Mössbauer isotope, such as, for example, $^{57}$Fe or $^{151}$Eu.

In the in vivo administration of the therapeutic agents according to the invention, the latter can be administered together with a suitable vehicle, such as, for example, serum, or physiological common salt solution and together with another protein, such as, for example, human serum albumin. In this case, the dosage depends on the type of cellular disorder, the metal ion used and the type of imaging method.

The therapeutic agents according to the invention are administered parenterally, preferably i.v.

Details of use of radiotherapeutic agents are discussed, e.g., in R. W. Kozak et al. TIBTEC, October 1986, 262.

The agents according to the invention are very well suited as x-ray contrast media, especially for computer tomography (CT), and it is especially to be emphasized that no signs of the anaphylaxis-like reactions, known from the iodine-containing contrast media, can be detected with them in biochemical-pharmacological studies. They are especially valuable because of the advantageous absorption properties in the areas of higher tube voltages for digital subtraction techniques.

In general, the agents according to the invention are dosed for use as x-ray contrast media analogously to, for example, meglumine-diatrizoate in amounts of 0.1–5 mmol/kg, preferably 0.25–1 mmol/kg.

Details of use of x-ray contrast media are discussed, for example, in Barke, Röntgenkontrastmittel [X-Ray Contrast Media], G. Thieme, Leipzig (1970) and P. Thurn, E. B ücheler "Einführung in die Röntgendiagnostik [Introduction to Diagnostic Radiology]," G. Thieme, Stuttgart, New York (1977).

In general, it has been possible to synthesize new complexing agents, metal complexes and metal complex salts, which open up new possibilities in diagnostic and therapeutic medicine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German Application No. 195 25 924.6, filed on Jul. 4, 1995, are hereby incorporated by reference.

EXAMPLE 1 a) Bis[2-(benzyloxycarbonylamino)-ethyl]-amine 51.5 g (500 mmol) of diethylenetriamine and 139 ml (1 mol) of triethylamine are dissolved in dichloromethane and mixed at −20° C. with 161 g of benzyl cyanoformate (Fluka) in dichloromethane and then stirred overnight at room temperature. After the reaction is completed, concentration by evaporation is performed during draw-off, the residue is taken up in diethyl ether, the organic phase is washed with sodium carbonate solution and dried with sodium sulfate. The filtrate is mixed with hexane, the precipitate is filtered out and dried.

Yield: 163.4 g (88% of theory)

| Elementary analysis: | | | |
|---|---|---|---|
| Cld: | C 64.67 | H 6.78 | N 11.31 |
| Fnd: | C 64.58 | H 6.83 | N 11.28 | b) N,N,N',N',N'',N''-Hexakis[2-(benzyloxycarbonylamino)-ethyl]-trimesic acid triamide 13.27 g (50 mmol) of trimesic acid trichloride (Aldrich) and 34.7 ml (250 mmol) of triethylamine are dissolved in dimethylformamide (DMF) and mixed at 0° C. with 65.0 g (175 mmol) of the amine described in Example 1a) and then stirred overnight at room temperature. The solution is concentrated by evaporation in a vacuum, and the residue is chromatographed on silica gel with ethyl acetate.

Yield: 39.4 g (62% of theory)

| Elementary analysis: | | | |
|---|---|---|---|
| Cld: | C 65.24 | H 5.95 | N 9.92 |
| Fnd: | C 65.54 | H 5.95 | N 9.87 | c) $N^\alpha,N^\varepsilon$-Bis(N,N'-dibenzyloxycarbonyl-lysyl)-lysine, protected "tri-lysine"

3.6 g (20 mmol) of lysine-hydrochloride and 6.95 ml (50 mmol) of triethylamine are dissolved in DMF, mixed with 26.8 g (50 mmol) of $N^{60},N^\varepsilon$-dibenzyloxycarbonyl-lysine-p-nitrophenylester (Bachem) and stirred for 2 days at room temperature. After the reaction is completed, it is concentrated by evaporation in a vacuum, the residue is taken up in ethyl acetate and shaken out with diluted hydrochloric acid. The organic phase is dried with sodium sulfate, the solvent is concentrated by evaporation, and the residue is chromatographed with ethyl acetate/ethanol in a step gradient.

Yield: 10.7 g (57% of theory)

| Elementary analysis: | | | |
|---|---|---|---|
| Cld: | C 63.95 | H 6.65 | N 8.95 |
| Fnd: | C 63.63 | H 6.69 | N 8.93 | d) Completely protected benzyloxycarbonyl-24-polyamine based on N,N,N',N',N'',N''-hexakis[2-(trilysyl-amino)-ethyl]-trimesic acid triamide 1.27 g (1 mmol) of the hexa-benzyloxycarbonylamine described in Example 1b) is dissolved in glacial acetic acid and mixed with 33% hydrogen bromide in glacial acetic acid while being stirred.

After 60 minutes, the incipient precipitation is completed with diethyl ether, the hexaamine-hydrobromide produced is washed with ether, dried in a vacuum and used in the subsequent reaction described below without further purification.

Yield: 0.95 g (quantitative)

7.0 g (7.5 mmol) of the protected "tri-lysine" described in Example 1c), 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 0.95 g (1 mmol) of the hexaamine-hydrobromide described above, and it is stirred overnight at room temperature. After the reaction is completed, it is concentrated by evaporation in a vacuum, and the residue is chromatographed on silica gel with ethyl acetate/ethanol (2:1).

Yield: 4.55 g (76% of theory)

| Elementary analysis: | | | |
|---|---|---|---|
| Cld: | C 64.35 | H 6.71 | N 10.52 |
| Fnd: | C 64.08 | H 6.57 | N 10.29 | e) 2-Bromopropionylglycine-benzyl ester 55.9 g (326.1 mmol) of 2-bromopropionic acid chloride is added in drops at 0° C. to 100 g (296.4 mmol) of glycine benzyl ester-p-toluenesulfonic acid salt and 33.0 g (326.1 mmol) of triethylamine in 400 ml of methylene chloride. The temperature is not allowed to exceed 5° C. After addition is completed, it is stirred for one hour at 0° C., then for 2 hours at room temperature. 500 ml of ice water is added, and the water phase is set at pH 2 with 10% aqueous hydrochloric acid. The organic phase is separated, washed once each with 300 ml of 5% aqueous soda solution and 400 ml of water. The organic phase is dried on magnesium sulfate and evaporated to dryness in a vacuum. The residue recrystallizes from diisopropyl ether.

Yield: 68.51 g (75% of theory) of a colorless crystalline powder

Melting point: 69°–70° C.

Elementary analysis:

| | | | | |
|---|---|---|---|---|
| Cld: | C 46.76 | H 7.19 | N 4.54 | Br 25.92 |
| Fnd: | C 46.91 | H 7.28 | N 4.45 | Br 25.81 | f) 1-[4-(Benzyloxycarbonyl)-1-methyl-2-oxo-3-azabutyl]-1,4,7,10-tetraazacyclododecane 50 g (162.2 mmol) of the title compound of Example 1e) is added to 55.8 g (324.4 mmol) of 1,4,7,10-tetraazacyclododecane, dissolved in 600 ml of chloroform, and it is stirred overnight at room temperature. 500 ml of water is added, the organic phase is separated and in each case washed twice with 400 ml of water. The organic phase is dried on magnesium sulfate and evaporated to dryness in a vacuum. The residue is chromatographed on silica gel (mobile solvent: chloroform/methanol/aqueous 25% ammonia=10:5:1).

Yield: 40.0 g [63% of theory relative to the 1e) used] of a slightly yellowish viscous oil.

Elementary analysis:

| | | | |
|---|---|---|---|
| Cld: | C 61.36 | H 8.50 | N 17.89 |
| Fnd: | C 61.54 | H 8.68 | N 17.68 | g) 10-[4-(Benzyloxycarbonyl)-1-methyl-2-oxo-3-azabutyl]-1,4,7-tris(tert-butoxycarbonylmethyl)-1,4,7,10-tetraazacyclododecane (sodium bromide complex)

33 g (169 mmol) of bromoacetic acid-tert-butyl ester is added to 20 g (51.08 mmol) of the title compound of Example 1f) and 17.91 g (169 mmol) of sodium carbonate in 300 ml of acetonitrile, and it is stirred for 24 hours at 60° C. It is cooled to 0° C., the salts are filtered out, and the filtrate is evaporated to dryness. The residue is chromatographed on silica gel (mobile solvent: ethyl acetate/ethanol: 15:1). The fractions that contain the product are concentrated by evaporation, and the residue recrystallizes from diisopropyl ether.

Yield: 34.62 g (81% of theory) of a colorless crystalline powder

Melting point: 116°–117° C.

Elementary analysis:

| | | | | | |
|---|---|---|---|---|---|
| Cld: | C 54.54 | H 7.59 | N 8.37 | Na 2.74 | Br 9.56 |
| Fnd: | C 54.70 | H 7.65 | N 8.24 | Na 2.60 | Br 9.37 | h) 10-(4-Carboxy-1-methyl-2-oxo-3-azabutyl)-1,4,7-tris(tert-butoxycarbonylmethyl)-1,4,7,10-tetraazacyclododecane (sodium bromide complex)

30 g (35.85 mmol) of the title compound of Example 1 g) is dissolved in 500 ml of isopropanol, and 3 g of palladium catalyst (10% Pd/C) is added. It is hydrogenated overnight at room temperature. Catalyst is filtered out, the filtrate is evaporated to dryness in a vacuum and recrystallized from acetone.

Yield: 22.75 g (85% of theory) of a colorless crystalline powder

Melting point: 225° C. (decomposition)

Elementary analysis:

| | | | | | |
|---|---|---|---|---|---|
| Cld: | C 49.86 | H 7.69 | N 9.38 | Na 3.07 | Br 10.71 |
| Fnd: | C 49.75 | H 7.81 | N 9.25 | Na 2.94 | Br 10.58 | i) 24-mer N-(5-DO3A-yl-4-oxo-3-azahexanoyl)-cascade polyamide based on N,N,N',N',N",N"-hexakis[2-(trilysylamino)-ethyl]-trimesic acid triamide*)

*) DO3A=1,4,7-tris(carboxymethyl)-1,4,7,10-tetraazacyclododecane 6.0 g (1 mmol) of the poly-benzyloxycarbonylamine described in Example 1d) is dissolved in glacial acetic acid and mixed with 33% hydrogen bromide in glacial acetic acid while being stirred. After 3 hours, the incipient precipitation is completed with diethyl ether, the 24-amine-hydrobromide produced is washed with ether and dried in a vacuum. 35.84 g (48 mmol) of the acid described in Example 1h) above is dissolved in DMF, mixed with 7.35 g (48 mmol) of 1-hydroxybenzotriazole, with 15.41 g (48 mmol) of TBTU (Peboc Limited, UK) and with 49.3 ml (288 mmol) of N-ethyldiisopropylamine, and it is stirred for 20 minutes at room temperature. This solution is then mixed with the (1 mmol) 24-amine-hydrobromide described above, and it is stirred for 4 days at room temperature. The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, set at pH 7, a YM3 Amicon®-ultrafiltration membrane is used to remove low-molecular portions, and the retentate is ultimately membrane-filtered and freeze-dried.

Yield: 13.5 g (83% of theory)

$H_2O$ content (Karl-Fischer): 6.2%

Elementary analysis (relative to anhydrous substance):

| | | | | |
|---|---|---|---|---|
| Cld: | C 45.82 | H 6.09 | N 15.07 | Na 10.79 |
| Fnd: | C 45.56 | H 6.15 | N 14.80 | Na 10.52 | k) 24-mer-Gd-complex of N-(5-DO3A-yl-4-oxo-3-azahexanoyl)-cascade polyamide based on N,N,N',N',N",N"-hexakis[2-(trilysylamino)-ethyl]-trimesic acid triamide 8.13 g (0.5 mmol) of the complexing agent acid described in Example 1i) above is set at pH 3 in water with diluted hydrochloric acid, mixed with 2.17 g (6 mmol) of $Gd_2O_3$, stirred for 30 minutes at 80° C., set at pH 7 after cooling and desalinated with a YM3 AMICON® ultrafiltration membrane. The retentate is ultimately membrane-filtered and freeze-dried.

Yield: 8.89 g (92.1% of theory)

$H_2O$ content (Karl-Fischer): 9.6%

Gd determination (AAS): 19.6%

Elementary analysis (relative to anhydrous substance):

| | | | | |
|---|---|---|---|---|
| Cld: | C 40.26 | H 5.35 | N 13.24 | Gd 21.62 |
| Fnd: | C 39.98 | H 5.51 | N 13.42 | Gd 21.37 |

Example 2 a) 2-Bromopropionyl-β-alanine-benzyl ester 53.65 g (313 mmol) of 2-bromopropionic acid chloride is added in drops at 0°C. to 100 g (285 mmol) of β-alanine-benzyl ester-p-toluenesulfonic acid salt and 31.67 g (313 mmol) of triethylamine in 400 ml of methylene chloride. The temperature is not allowed to exceed 5° C. After addition is completed, it is stirred for 1 hour at 0° C., then for 2 hours at room temperature. 500 ml of ice water is added, and the water phase is set at pH 2 with 10% aqueous hydrochloric acid. The organic phase is separated, washed once each with 300 ml of 5% aqueous hydrochloric acid, 300 ml of 5% aqueous soda solution and 400 ml of water. The organic phase is dried on magnesium sulfate and evaporated to dryness in a vacuum. The residue recrystallizes from diisopropyl ether.

Yield: 71.36 g (78% of theory) of a colorless crystalline powder

| Elementary analysis: | | | | |
|---|---|---|---|---|
| Cld: | C 48.46 | H 7.51 | N 4.35 | Br 24.80 |
| Fnd: | C 48.29 | H 7.65 | N 4.25 | Br 24.61 | b) 1-[5-(Benzyloxycarbonyl)-1-methyl-2-oxo-3-azapentyl]-1,4,7,10-tetraazacyclododecane 50 g (155.2 mmol) of the title compound of Example 2a) is added to 53.32 g (310 mmol) of 1,4,7,10-tetraazacyclododecane dissolved in 600 ml of chloroform, and it is stirred overnight at room temperature. 500 ml of water is added, the organic phase is separated, and it is washed twice in each case with 400 ml of water. The organic phase is dried on magnesium sulfate and evaporated to dryness in a vacuum. The residue is chromatographed on silica gel (mobile solvent: chloroform/methanol/aqueous 25% ammonia: 10/5/1).

Yield: 38.39 g [61% of theory relative to the 2a) used] of a light yellowish viscous oil.

| Elementary analysis: | | | |
|---|---|---|---|
| Cld: | C 62.20 | H 8.70 | N 17.27 |
| Fnd: | C 62.05 | H 8.81 | N 17.15 | c) 10-[5-(Benzyloxycarbonyl)-1-methyl-2-oxo-3-azapentyl]-1,4,7-tris(tert-butoxycarbonyl-methyl)-1,4,7,10-tetraazacyclododecane (sodium bromide complex)

31.8 g (163 mmol) of bromoacetic acid-tert-butyl ester is added to 20 g (49.32 mmol) of the title compound of Example 2b) and 17.28 g (163 mmol) of sodium carbonate in 300 ml of acetonitrile, and it is stirred for 24 hours at 60° C. It is cooled to 0° C., salts are filtered out, and the filtrate is evaporated to dryness. The residue is chromatographed on silica gel (mobile solvent: ethyl acetate/ethanol=10/1). The fractions that contain the product are concentrated by evaporation, and the residue recrystallizes from diisopropyl ether.

Yield: 31.89 g (76% of theory) of a colorless, crystalline powder

| Elementary analysis: | | | | | |
|---|---|---|---|---|---|
| Cld: | C 55.05 | H 7.70 | N 8.23 | Na 2.69 | Br 9.40 |
| Fnd: | C 55.17 | H 7.85 | N 8.10 | Na 2.51 | Br 9.30 | d) 10-[5-(Carboxy)-1-methyl-2-oxo-3-azapentyl]-1,4,7-tris(tert-butoxycarbonylmethyl)-1,4,7,10-tetraazacyclododecane (sodium bromide complex)

30 g (35.26 mmol) of the title compound of Example 2c) is dissolved in 500 ml of isopropanol, and 3 g of palladium catalyst (10% Pd/C) is added. It is hydrogenated overnight at room temperature. Catalyst is filtered out, the filtrate is evaporated to dryness in a vacuum and recrystallized from acetone.

Yield: 24.41 g (91% of theory) of a colorless, crystalline powder

| Elementary analysis: | | | | | |
|---|---|---|---|---|---|
| Cld: | C 50.52 | H 7.82 | N 9.21 | Na 3.01 | Br 10.52 |
| Fnd: | C 50.41 | H 7.95 | N 9.10 | Na 2.91 | Br 10.37 | e) 24-mer N-(6-DO3A-yl-5-oxo-4-azaheptanoyl)-cascade polyamide based on N,N,N',N',N",N"-hexakis[2-(trilysylamino)-ethyl]-trimesic acid triamide 6.0 g (1 mmol) of the poly-benzyloxycarbonylamine described in Example 1d) is dissolved in glacial acetic acid and mixed with 33% hydrogen bromide in glacial acetic acid while being stirred. After 3 hours, the incipient precipitation is completed with diethyl ether, the 24-amine-hydrobromide produced is washed with ether and dried in a vacuum.

36.52 g (48 mmol) of the acid described in Example 2d) above is dissolved in DMF, mixed with 7.35 g (48 mmol) of 1-hydroxybenzotriazole, with 15.41 g (48 mmol) of TBTU (Peboc Limited, UK) and with 49.3 ml (288 mmol) of N-ethyldiisopropylamine, and it is stirred for 20 minutes at room temperature. This solution is then mixed with the (1 mmol) 24-amine-hydrobromide described above and stirred for 4 days at room temperature. The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, set at pH 7, a YM3 Amicon® ultrafiltration membrane is used to remove low-molecular portions, and the retentate is ultimately membrane-filtered and freeze-dried.

Yield: 14.4 g (85% of theory)
$H_2O$ content (Karl-Fischer): 8.7%

| Elementary analysis (relative to anhydrous substance): | | | | |
|---|---|---|---|---|
| Cld: | C 46.82 | H 5.98 | N 14.79 | Na 10.59 |
| Fnd: | C 47.04 | H 6.23 | N 14.96 | Na 10.26 | f) 24-mer-Gd Complex of N-(6-DO3A-yl-5-oxo-4-azaheptanoyl)-cascade polyamide based on N,N,N',N',N",N"-hexakis[2-(trilysylamino)-ethyl]-trimesic acid triamide 8.5 g (0.5 mmol) of the complexing agent acid described in Example 2e) above is set at pH 3 in water with diluted hydrochloric acid, mixed with 2.17 g (6 mmol) of $Gd_2O_3$, stirred for 30 minutes at 80° C., set at pH 7 after cooling and desalinated with a YM3 AMICON® ultrafiltration membrane. The retentate is ultimately membrane-filtered and freeze-dried.

Yield: 8.50 g (88% of theory)
$H_2O$ content (Karl-Fischer): 7.9%
Gd determination (AAS): 19.4%

| Elementary analysis (relative to anhydrous substance): | | | | |
|---|---|---|---|---|
| Cld: | C 41.12 | H 5.52 | N 12.99 | Gd 21.21 |
| Fnd: | C 40.86 | H 5.34 | N 13.25 | Gd 20.95 |

EXAMPLE 3 a) N,N'-Bis(benzyloxycarbonyl)-3-[carboxymethoxyacetyl]-3-azapentane-1,5-diamine 37.14 g (100 mmol) of the bis(benzyloxycarbonyl-aminoethyl)-amine described in Example 1a) is dissolved in DMF, mixed in an ice bath with 17.4 g (150 mmol) of diglycolic anhydride (Janssen Chimica) and 21 ml (150 mmol) of triethylamine and then stirred overnight at room temperature. The solution is concentrated by evaporation in a vacuum, the residue is taken up in ethyl acetate and shaken out with diluted hydrochloric acid. The organic phase is dried with sodium sulfate and after the drying agent is filtered, it is crystallized by adding hexane.

Yield: 41.4 g (85% of theory)

| Elementary analysis: | | | |
|---|---|---|---|
| Cld: | C 59.13 | H 6.00 | N 8.62 |
| Fnd: | C 58.99 | H 5.93 | N 8.70 | b) N,N',N'',N'''-Tetrakis{8-(benzyloxycarbonylamino)-6-[2-(benzyloxycarbonylaminoethyl]-5-oxo-3-oxaoctanoyl}cyclene 345 mg (2 mmol) of 1,4,7,10-tetraazacyclododecane (cyclene; Fluka) is azeotropically dehydrated with toluene. A solution of 4.88 g (10 mmol) of N,N'-bis(benzyloxycarbonyl)-3-[carboxymethoxyacetyl]-3-azapentane-1,5-diamine [Example 3a)] in tetrahydrofuran (THF) as well as 2.47 g (10 mmol) of 2-ethoxy-1-ethoxycarbonyl-1,2-dihydroquinoline (EEDQ; Fluka) are added to the cooled solution of cyclene in toluene at room temperature, and it is stirred overnight. After the reaction is completed, the product is precipitated by adding hexane, decanted from solvent and reprecipitated once more from THF/hexane and then from THF/toluene. After drying in a vacuum, 2.78 g (68% of theory) of a pale yellow solid is obtained.

| Elementary analysis: | | | |
|---|---|---|---|
| Cld: | C 60.93 | H 6.29 | N 10.93 |
| Fnd: | C 60.68 | H 6.40 | N 10.97 | c) Completely protected benzyloxycarbonyl-32-polyamine based on 32-amine condensed with N$^\alpha$,N$^\epsilon$-bis(lysyl)-lysine ("tri-lysine) from N,N',N'',N'''-tetrakis{8-benzyloxycarbonylamino)-6-[2-(benzyloxycarbonylamino)-ethyl]-5-oxo-3-oxaoctanoyl}cyclene 2.05 g (1 mmol) of the octa-benzyloxycarbonylamine described in Example 3b) is dissolved in glacial acetic acid and mixed with 33% hydrogen bromide in glacial acetic acid while being stirred. After 90 minutes, the incipient precipitation is completed with diethyl ether, the octa-amine-hydrobromide produced is washed with ether, dried in a vacuum and used in the subsequent reaction described below without further purification.

Yield: 1.6 g (quantitative)

9.4 g (10 mmol) of the protected "tri-lysine" described in Example 1c), 1.5 g (10 mmol) of 1-hydroxybenzotriazole and 3.2 g (10 mmol) of 2-(1H-benzotriazol-1-yl)-1,1,3,3,-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 1.6 g (1 mmol) of the octaamine-hydrobromide described above, and it is stirred overnight at room temperature. After the reaction is completed, it is concentrated by evaporation in a vacuum, and the residue is chromatographed on silica gel with dichloromethane/methanol (10:1).

Yield: 6.0 g (72% of theory)

| Elementary analysis: | | | |
|---|---|---|---|
| Cld: | C 63.32 | H 6.76 | N 10.74 |
| Fnd: | C 62.98 | H 6.91 | N 10.43 | d) 32-mer N-(5-DO3A-yl-4-oxo-3-azahexanoyl)-cascade polyamide based on the 32-mer amine described in Example 3c) above 8.35 g (1 mmol) of the 32-mer-benzyloxycarbonylamine described in Example 3c) is dissolved in glacial acetic acid and mixed with 33% hydrogen bromide in glacial acetic acid while being stirred. After 3 hours, the incipient precipitation is completed with diethyl ether, the 32-amine-hydrobromide produced is washed with ether and dried in a vacuum.

47.8 g (64 mmol) of the acid described in Example 1h) is dissolved in DMF, mixed with 9.8 g (64 mmol) of 1-hydroxybenzotriazole, with 20.5 g (64 mmol) of TBTU (Peboc Limited, UK) and with 65.7 ml (384 mmol) of N-ethyldiisopropylamine, and it is stirred for 20 minutes at room temperature. This solution is then mixed with the (1 mmol) 32-amine-hydrobromide described above and stirred for 4 days at room temperature. The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, set at pH 7, a YM3 Amicon® ultrafiltration membrane is used to remove low-molecular portions, and the retentate is ultimately membrane-filtered and freeze-dried.

Yield: 17.2 g (76.4% of theory)
H$_2$O content (Karl-Fischer): 7.6%

| Elementary analysis (relative to anhydrous substance): | | | | |
|---|---|---|---|---|
| Cld: | C 45.73 | H 6.12 | N 15.08 | Na 10.61 |
| Fnd: | C 45.89 | H 6.30 | N 14.84 | Na 10.31 | e) 32-mer-Gd Complex of N-(5-DO3A-yl-4-oxo-3-azahexanoyl)-cascade polyamide based on the 32-mer amine described in Example 3c)

10.4 g (0.5 mmol) of the complexing agent acid described in Example 3d) above is set at pH 3 in water with diluted hydrochloric acid, mixed with 2.89 g (8 mmol) of Gd$_2$O$_3$, stirred for 30 minutes at 80° C., set at pH 7 after cooling and desalinated with a YM3 AMICON® ultrafiltration membrane. The retentate is ultimately membrane-filtered and freeze-dried.

Yield: 12.1 g (91.1% of theory)
H$_2$O content (Karl-Fischer): 11.0%
Gd determination (AAS): 18.6%

| Elementary analysis (relative to anhydrous substance): | | | | |
|---|---|---|---|---|
| Cld: | C 40.26 | H 5.39 | N 13.28 | Gd 21.30 |
| Fnd: | C 40.10 | H 5.21 | N 13.04 | Gd 21.03 |

The ytterbium complex is obtained analogously with Yb$_2$(CO$_3$)$_3$:

| Elementary analysis (relative to anhydrous substance): | | | |
|---|---|---|---|
| Cld: C 39.42 | H 5.28 | N 13.00 | Yb 22.94 |
| Fnd: C 39.29 | H 5.40 | N 12.81 | Yb 22.65 |

EXAMPLE 4 a) Hexaethylene glycol monomethyl ether-p-toluenesulfonic acid ester 14.3 g (75 mmol) of p-toluenesulfonic acid chloride is added in portions at 0° C. to 20 g (67.49 mmol) of hexaethylene glycol monomethyl ether and 7.59 g (75 mmol) of triethylamine in 200 ml of chloroform, and it is then stirred for 4 hours at this temperature. It is evaporated to dryness in a vacuum, and the residue is chromatographed on silica gel (mobile solvent: chloroform/methanol=5/1).

Yield: 27.67 g (91% of theory) of a sheetlike, vitreous solid

| Elementary analysis: | | |
|---|---|---|
| Cld: C 53.32 | H 7.61 | S 7.12 |
| Fnd: C 53.15 | H 7.70 | S 7.03 | b) 1-Benzyloxy-5-(benzyloxycarbonyl)-2-chloro-3-oxo-4-azapentane 76 g (326.1 mmol) of 2-chloro-3-(benzyloxy)-propionic acid chloride (produced according to Inorg. Chem. Vol. 31; 2422, 1992) is added in drops to 100 g (296.4 mmol) of glycine benzyl ester-p-toluenesulfonic acid salt and 33.0 g (326.1 mmol) of triethylamine in 400 ml of methylene chloride at 0° C., and it is stirred for 2 hours at this temperature. 500 ml of ice water is added, and the water phase is set at pH 2 with 10% aqueous hydrochloric acid. The organic phase is separated, washed once each with 300 ml of 5% aqueous hydrochloric acid, 300 ml of 5% aqueous soda solution and 400 ml of water. The organic phase is dried on magnesium sulfate and evaporated to dryness in a vacuum. The residue is chromatographed on silica gel (mobile solvent: methylene chloride/hexane/acetone=15/5/1).

Yield: 75.07 g (70% of theory) of a pale yellow-colored viscous oil

| Elementary analysis: | | | |
|---|---|---|---|
| Cld: C 63.07 | H 5.57 | N 3.87 | Cl 9.80 |
| Fnd: C 63.17 | H 5.65 | N 3.75 | Cl 9.63 | c) 1-[4-(Benzyloxycarbonyl)-1-(benzyloxymethyl)-2-oxo-3-azabutyl]-1,4,7,10-tetraazacyclododecane 70 g (193.5 mmol) of the title compound of Example 4b) and 11.1 g (64.5 mmol) of 1,4,7,10-tetraazacyclododecane are dissolved in 70 ml of dimethylformamide and stirred for 2 days at 50° C. It is evaporated to dryness in a vacuum, the residue is taken up in 700 ml of water and extracted twice with 250 ml of chloroform each. The organic phase is dried on magnesium sulfate and evaporated to dryness in a vacuum. The residue is chromatographed on silica gel (mobile solvent: chloroform/methanol/25% aqueous ammonia=10/5/1).

Yield: 13.16 g (41% of theory relative to cyclene) of a viscous, colorless oil

| Elementary analysis: | | |
|---|---|---|
| Cld: C 65.17 | H 7.90 | N 14.07 |
| Fnd: C 65.24 | H 7.77 | N 14.18 | d) 10-[4-(Benzyloxycarbonyl)-1-(benzyloxymethyl)-2-oxo-3-azabutyl]-1,4,7-tris(tert-butoxycarbonylmethyl)-1,4,7,10-tetraazacyclododecane (sodium bromide complex)

16.81 g (86.2 mmol) of bromoacetic acid-tert-butyl ester is added to 13 g (26.12 mmol) of the title compound of Example 4c) and 9.14 g (86.2 mmol) of sodium carbonate in 200 ml of acetonitrile, and it is stirred for 24 hours at 60° C. It is cooled to 0° C., salts are filtered out, and the filtrate is evaporated to dryness. The residue is chromatographed on silica gel (mobile solvent: ethyl acetate/ethanol=15/1).

Yield: 19.46 g (79% of theory) of a waxy solid

| Elementary analysis: | | | | |
|---|---|---|---|---|
| Cld: C 57.32 | H 7.38 | N 7.43 | Na 2.43 | Br 8.47 |
| Fnd: C 57.22 | H 7.51 | N 7.27 | Na 2.33 | Br 8.29 | e) 10-[4-Carboxy-2-oxo-1-hydroxymethyl-3-azabutyl]-1,4,7-tris(tert-butoxycarbonylmethyl)-1,4,7,10-tetraazacyclododecane (sodium bromide complex)

3 g of palladium catalyst (10% Pd/C) is added to 19 g (20.15 mmol) of the title compound of Example 4d) in 300 ml of isopropanol and hydrogenated overnight at room temperature. Catalyst is filtered out, the filtrate is evaporated to dryness in a vacuum, and the residue recrystallizes from acetone.

Yield: 13.06 g (85% of theory) of a colorless, crystalline powder

| Elementary analysis: | | | | |
|---|---|---|---|---|
| Cld: C 48.82 | H 7.53 | N 9.18 | Na 3.00 | Br 10.49 |
| Fnd: C 48.71 | H 7.68 | N 9.03 | Na 2.81 | Br 10.23 | f) 10[4-(Benzyloxycarbonyl)-1-(hydroxymethyl)-2-oxo-3-azabutyl]-1,4,7-tris(tert-butoxy-carbonylmethyl)-1,4,7,10-tetraazacyclododecane 3.42 g (20 mmol) of benzyl bromide is added to 13 g (17.04 mmol) of the title compound of Example 4e) and 6.11 g (18.75 mmol) of anhydrous cesium carbonate in 70 ml of dimethylformamide, and it is stirred overnight at 50° C. It is cooled to 0° C., and 700 ml of water is added. Then, it is extracted twice with 300 ml of methylene chloride each. The combined organic phases are washed twice with water, dried on magnesium sulfate and evaporated to dryness in a vacuum. The residue is chromatographed on silica gel (mobile solvent: ethyl acetate/ethanol).

Yield: 9.97 g (78% of theory) of a colorless, viscous oil

| Elementary analysis: | | |
|---|---|---|
| Cld: C 60.86 | H 8.47 | N 9.34 |
| Fnd: C 60.95 | H 8.61 | N 9.21 | g) 10-[4-(Benzyloxycarbonyl)-1-(2,5,8,11,14,17,20-heptaoxa-heneicosanoyl)-2-oxo-3-azabutyl]-1,4,7-tris(tert-butoxycarbonylmethyl)-1,4,7,10-tetraazacyclododecane 9.7 g (12.93 mmol) of the title compound of Example 4f) is dissolved in 50 ml of THF, and 0.43 g (14.22 mmol) of sodium hydride (80% in paraffin) is added at −10° C. It is stirred for 30 minutes at 0° C. Then, 11.65 g (25.86 mmol) of the title compound of Example 4a) and 3.46 g (25.86 mmol) of lithium iodide are added. It is stirred for 24 hours at room temperature. 3 ml of water is carefully added and then evaporated to dryness. The residue is chromatographed on silica gel (mobile solvent: chloroform/methanol=10:1).

Yield: 12.1 g (91% of theory) of a vitreous solid

| Elementary analysis: | | | |
|---|---|---|---|
| Cld: | C 59.57 | H 8.72 | N 6.81 |
| Fnd: | C 59.65 | H 8.91 | N 6.62 | h) 10-[1-(2-8,11,14,17,20-Heptaoxa-heneicosanoyl)-2-oxo-3-aza-4-(carboxy)-butyl]-1,4,7-tris(tert-butoxycarbonylmethyl)-1,4,7,10-tetraazacyclododecane 12 g (11.67 mmol) of the title compound of Example 4g) is dissolved in 300 ml of isopropanol and 2 g of palladium catalyst (10% Pd/C) is added. It is hydrogenated overnight at room temperature. Catalyst is filtered out, and the filtrate is evaporated to dryness. The residue recrystallizes from acetone/diisopropyl ether.

Yield: 10.18 g (93% of theory) of a waxy solid

| Elementary analysis: | | | |
|---|---|---|---|
| Cld: | C 56.33 | H 8.92 | N 7.46 |
| Fnd: | C 56.20 | H 9.03 | N 7.35 | i) 24-mer Gd complex of N-(5-DO3A-yl-4-oxo-3-aza-7,10,13,16,19,22,25-heptaoxa-hexacosanoyl)-cascade polyamide based on N,N,N',N',N'',N''-hexakis[2-(trilysylamino)-ethyl]-trimesic acid triamide 6.0 g (1 mmol) of the 24- mer-benzyloxycarbonylamine described in Example 1d) is dissolved in glacial acetic acid and mixed with 33% hydrogen bromide in glacial acetic acid while being stirred. After 3 hours, the incipient precipitation is completed with diethyl ether, the 24-amine-hydrobromide produced is washed with ether and dried in a vacuum. 45.03 g (48 mmol) of the acid described in Example 4h) above is dissolved in DMF, mixed with 7.35 g (48 mmol) of 1-hydroxybenzotriazole, with 15.41 g (48 mmol) of TBTU (Peboc Limited, UK) and with 49.3 ml (288 mmol) of N-ethyldiisopropylamine and stirred for 20 minutes at room temperature. This solution is then mixed with the above described (1 mmol) 24-amine hydrobromide and stirred for 4 days at room temperature. The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, set at pH 3 with diluted hydrochloric acid, mixed with 8.70 g (24 mmol) of $Gd_2O_3$, stirred for 4 hours at 80° C., set at pH 7 after cooling, and a YM3 AMICON® ultrafiltration membrane is used to remove low-molecular portions, and the retentate is ultimately membrane-filtered and freeze-dried.

Yield: 19.6 g (73.3% of theory)
$H_2O$ content (Karl-Fischer): 8.3%
Gd determination (AAS): 14.0%

| Elementary analysis (relative to anhydrous substance): | | | | |
|---|---|---|---|---|
| Cld: | C 43.94 | H 6.38 | N 9.43 | Gd 15.39 |
| Fnd: | C 44.27 | H 6.22 | N 9.29 | Gd 15.09 |

EXAMPLE 5 a) 1,7-Bis(trifluoroacetyl)-1,4,7-triazaheptane 113.3 g (790 mmol) of trifluoroacetic acid ethyl ester is added in drops to a solution consisting of 41.14 g (390 mmol) of 1,4,7-triazaheptane in 350 ml of tetrahydrofuran at 80° C. and under nitrogen. It is allowed to stir overnight at room temperature, concentrated by evaporation in a vacuum. The remaining oil is crystallized from hexane.

Yield: 115 g (99.9% of theory)
Melting point: 68°–70° C.

| Elementary analysis: | | | | |
|---|---|---|---|---|
| Cld: | C 32.55 | H 3.76 | F 38.62 | N 14.24 |
| Fnd: | C 32.63 | H 3.75 | F 38.38 | N 14.19 | b) 1,7-Bis(trifluoroacetyl)-4-benzyloxycarbonyl-1,4,7-triazaheptane 14.75 g (50 mmol) of the trifluoroacetyl compound produced under Example 5a) as well as 8.3 ml (60 mmol) of triethylamine are dissolved in 120 ml of dichloromethane and cooled to 0° C. While being stirred, 7.5 ml (53 mmol) of benzyl chloroformate (97%), dissolved in 20 ml of dichloromethane, is now added in drops. It is allowed to stir overnight at room temperature, the salts are extracted with distilled water, the dichloromethane solution is dried on sodium sulfate, evaporated to dryness in a vacuum, and the residue is crystallized from ether/hexane.

Yield: 18.40 g (85.7% of theory)
Melting point: 131°–132° C.

| Elementary analysis: | | | | |
|---|---|---|---|---|
| Cld: | C 44.76 | H 3.99 | F 26.55 | N 9.79 |
| Fnd: | C 44.87 | H 4.03 | F 26.62 | N 9.61 | c) 3,9-Bis(tert-butoxycarbonylmethyl)-6-benzyloxycarbonyl-3,6,9-triazaundecanedicarboxylic acid-di-tert-butyl ester 4.29 g (10 mmol) of the trifluoroacetyl derivative produced under Example 5b) is dissolved in 30 ml of ethanol and mixed with 800 mg (20 mmol) of sodium hydroxide solution in 10 ml of distilled water. It is stirred for 3 hours at room temperature, evaporated to dryness in a vacuum at 40° C. bath temperature, residual water is removed by azeotropic distillation with isopropanol and taken up in 30 ml of dimethylformamide. 6.9 g (50 mmol) of potassium carbonate as well as 9.7 g (50 mmol) of bromoacetic acid-tert-butyl ester are then added to it, and the 4-benzyloxycarbonyl-1,4,7-triazaheptane is alkylated at room temperature overnight. The dimethylformamide is then drawn off in an oil pump vacuum, the residue is dispersed between water and dichloromethane, the organic solution is dried on sodium sulfate, evaporated to dryness in a vacuum, and the residue is purified by chromatography on silica gel. The title compound is eluted with ethyl acetate/hexane. It is obtained as foam.

Yield: 6.49 g (93.6% of theory)

| Elementary analysis: | | | |
|---|---|---|---|
| Cld: | C 62.32 | H 8.57 | N 6.06 |
| Fnd: | C 62.41 | H 8.66 | N 6.01 | d) 3,9-Bis(tert-butoxycarbonylmethyl)-3,6,9-triazaundecanedicarboxylic acid-di-tert-butyl ester 3.5 g (5 mmol) of the compound produced under Example 5c) is dissolved in 100 ml of ethanol, mixed with 200 mg of Pearlman's catalyst (Pd 20% on activated carbon) and hydrogenated until the calculated amount of hydrogen is taken up. Catalyst is suctioned off and evaporated to dryness in a vacuum. The title compound is obtained as white foam.

Yield: 2.80 g (99.9% of theory)

| Elementary analysis: | | | |
|---|---|---|---|
| Cld: | C 60.08 | H 9.54 | N 7.51 |
| Fnd: | C 60.02 | H 9.62 | N 7.56 | e) 3,9-Bis(tert-butoxycarbonylmethyl)-6-[1-(ethoxycarbonyl)-ethyl]-3,6,9-triazaundecanedioic acid-di-tert-butyl ester 5.60 g (10 mmol) of the amino compound produced under Example 5d) is dissolved in 30 ml of dimethylformamide. 1.66 g (12 mmol) of potassium carbonate as well as 2.17 g (12 mmol) of 2-bromopropionic acid ethyl ester are then added to it at room temperature, and it is stirred overnight. It is then poured on ice water, extracted with ethyl acetate, the organic solution is dried on sodium sulfate, evaporated to dryness in a vacuum, and the title compound is obtained by chromatography on silica gel. A mixture of ethyl acetate/hexane is used as eluant.

Yield: 4.18 g (63.4% of theory)

| Elementary analysis: | | | |
|---|---|---|---|
| Cld: | C 60.07 | H 9.32 | N 6.37 |
| Fnd: | C 60.18 | H 9.40 | N 6.31 | f) 3,9-Bis(tert-butoxycarbonylmethyl)-6-[1-(carboxy)-ethyl]-3,6,9-triazaundecanedioic acid-di-tert-butyl ester 6.60 g (10 mmol) of the compound produced under Example 5e) is dissolved in 50 ml of ethanol. The solution of 400 mg (10 mmol) of sodium hydroxide in 5 ml of distilled water is then added to it and stirred for 3 hours at 50° C. According to the thin-layer chromatogram, the saponification is quantitative. It is evaporated to dryness in a vacuum, traces of water are removed by codistillation with ethanol, and the residue is dried at 40° C. in a vacuum. The title compound is obtained as white powder. The remaining white residue is dissolved in 80 ml of wet ethanol (9:1) and mixed with the solution of 535 mg (10 mmol) of ammonium chloride in 10 ml of distilled water while being stirred. It is evaporated to dryness in a vacuum, the soluble portions in butanol are taken up and again evaporated to dryness in a vacuum. The residue is extracted with toluene. The organic solution is evaporated to dryness in a vacuum, and the title compound is obtained as foam.

Yield: 5.35 g (84.7% of theory)

| Elementary analysis: | | | |
|---|---|---|---|
| Cld: | C 58.93 | H 9.09 | N 6.65 |
| Fnd: | C 59.01 | H 9.16 | N 6.60 | g) 24-mer N-{N,N-bis[2-(N,N-bis(carboxymethyl))-aminoethyl]-alanyl}-cascade-polyamide based on N,N,N',N',N'',N''-hexakis[2-(trilysylamino)-ethyl]-trimesic acid triamide, sodium salt 6.0 g (1 mmol) of the poly-benzyloxycarbonylamine described in Example 1d) is dissolved in glacial acetic acid and mixed with 33% hydrogen bromide in glacial acetic acid while being stirred. After 3 hours, the incipient precipitation is completed with diethyl ether, the 24-amine-hydrobromide produced is washed with ether and dried in a vacuum. 30.33 g (48 mmol) of the acid described in Example 5f) above is dissolved in DMF, mixed with 7.35 g (48 mmol) of 1-hydroxybenzotriazole, with 15.41 g (48 mol) of TBTU (Peboc Limited, UK) and with 49.3 ml (288 mmol) of N-ethyldiisopropylamine, and it is stirred for 20 minutes at room temperature. This solution is then mixed with the (1 mmol) 24-amine-hydrobromide described above, and it is stirred for 4 days at room temperature. The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, set at pH 7, a YM3 Amicon® ultrafiltration membrane is used to remove low-molecular portions, and the retentate is ultimately membrane-filtered and freeze-dried.

Yield: 11.0 g (86.3% of theory)
H$_2$O content (Karl-Fischer): 8.2%

| Elementary analysis (relative to anhydrous substance): | | | | |
|---|---|---|---|---|
| Cld: | C 42.87 | H 5.41 | N 11.96 | Na 12.08 |
| Fnd: | C 42.78 | H 5.66 | N 12.11 | Na 11.89 | h) 24-mer-Gd complex of N-{N,N-bis(carboxymethyl))-aminoethyl]-alanyl}-cascade polyamide based on N,N,N',N',N'',N''-hexakis[2-(trilysylamino)-ethyl]-trimesic acid triamide, sodium salt 8.13 g (0.5 mmol) of the complexing agent acid described in Example 5g) above is set at pH 3 in water with diluted hydrochloric acid, mixed with 2.17 g (6 mmol) of Gd$_2$O$_3$, stirred for 30 minutes at 80° C., set at pH 7 after cooling and desalinated with a YM3 AMICON® ultrafiltration membrane. The retentate is ultimately membrane-filtered and freeze-dried.

Yield: 8.0 g (90.5% of theory)
H$_2$O content (Karl-Fischer): 7.5%
Gd determination (AAS): 21.0%

| Elementary analysis (relative to anhydrous substance): | | | | |
|---|---|---|---|---|
| Cld: | C 35.93 | H 4.38 | N 10.03 | Gd 23.09 | Na 3.38 |
| Fnd: | C 35.71 | H 4.65 | N 9.88 | Gd 22.84 | Na 3.50 |

EXAMPLE 6 a) 3,9-Bis(tert-butoxycarbonylmethyl)-6-benzyloxycarbonylmethyl-3,6,9-triazaundecanedioic acid-di-tert-butyl ester 5.60 g (10 mmol) of the amino compound produced under Example 5d) is dissolved in 30 ml of dimethylformamide. 1.66 g (12 mmol) of potassium carbonate as well as 2.58 g (12 mmol) of bromoacetic acid benzyl ester are then added to it and stirred overnight. It is then poured onto ice water, extracted with ethyl acetate, the organic solution is dried on sodium sulfate, evaporated to dryness in a vacuum, and the title compound is obtained by chromatography on silica gel. A mixture of ethyl acetate/hexane is used as eluant.

Yield: 6.32 g (89.3% of theory)

| Elementary analysis: | | | |
|---|---|---|---|
| Cld: | C 64.65 | H 9.00 | N 5.95 |
| Fnd: | C 64.62 | H 9.07 | N 5.90 | b) 3,9-Bis(tert-butoxycarbonylmethyl)-6-carboxymethyl-3,6,9-triazaundecanedioic acid-di-tert-butyl ester 7.08 g (10 mmol) of the benzyl ester produced under 6a) is dissolved in 100 ml of ethanol and mixed with 0.4 g of Pearlman's catalyst (Pd 20%, C). It is hydrogenated until 224 ml of hydrogen is taken up, catalyst is suctioned out, rewashed well with ethanol, and the solution is evaporated to dryness in a vacuum. The product is obtained as foam, which crystallizes from ether/hexane.

Yield: 6.87 g (97.3% of theory)
Melting point: 73°–75° C.

| Elementary analysis: | | | |
|---|---|---|---|
| Cld: | C 57.85 | H 9.00 | N 5.95 |
| Fnd: | C 57.91 | H 9.11 | N 6.01 | c) 32-mer N-{N,N-Bis[2-(N,N-bis(carboxymethyl))-aminoethyl]-glycyl}-cascade-polyamide based on the 32-mer amine described in Example 3c), sodium salt 8.35 g (1 mmol) of the 32-mer-benzyloxycarbonylamine described in Example 3c) is dissolved in glacial acetic acid and mixed with 33% hydrogen bromide in glacial acetic acid while being stirred. After 3 hours, the incipient precipitation is completed with diethyl ether, the 32-amine-hydrobromide produced is washed with ether and dried in a vacuum.

39.5 g (64 mmol) of the acid described in Example 6b) above is dissolved in DMF, mixed with 9.8 g (64 mmol) of 1-hydroxybenzotriazole, with 20.5 g (64 mmol) of TBTU (Peboc Limited, UK) and with 65.7 ml (384 mmol) of N-ethyldiisopropylamine, and it is stirred for 20 minutes at room temperature. This solution is then mixed with the (1 mmol) 32-amine-hydrobromide described above, and it is stirred for 4 days at room temperature. The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, set at pH 7, a YM3 Amicon® ultrafiltration membrane is used to remove low-molecular portions, and the retentate is ultimately membrane-filtered and freeze-dried.

Yield: 15.7 g (78.6% of theory)
H$_2$O content (Karl-Fischer): 9.0%

| Elementary analysis (relative to anhydrous substance): | | | | |
|---|---|---|---|---|
| Cld: | C 41.77 | H 5.24 | N 12.33 | Na 12.14 |
| Fnd: | C 41.49 | H 5.36 | N 12.49 | Na 11.93 | d) 32-mer-Gd-complex of the N-{N,N-bis[2-(N,N-bis(carboxymethyl)-aminoethyl]-glycyl}-cascade polyamide based on the 32-mer amine described in Example 3c), sodium salt 10.0 g (0.5 mmol) of the complexing agent acid described in Example 6c) above is set at pH 3 in water with diluted hydrochloric acid, mixed with 2.89 g (8 mmol) of Gd$_2$O$_3$, stirred for 30 minutes at 80° C., set at pH 7 after cooling and desalinated with a YM3 AMICON® ultrafiltration membrane. The retentate is ultimately membrane-filtered and freeze-dried.

Yield: 10.9 g (90.9% of theory)
H$_2$O content (Karl-Fischer): 9.5%
Gd determination (AAS): 20.9%

| Elementary analysis (relative to anhydrous substance): | | | | | |
|---|---|---|---|---|---|
| Cld: | C 34.98 | H 4.24 | N 10.33 | Gd 23.19 | Na 3.39 |
| Fnd: | C 35.20 | H 4.08 | N 10.46 | Gd 22.89 | Na 3.60 |

Example for an In Vivo Comparison with an Extracellular Contrast Medium

The suitability of the compound described in Example 1k) blood-pool-agent is shown in the following test.

As test animals, five male (Schering-SPF) rats that are 300–350 g in weight are used. Before the test, the abdomen is opened, the intestines are shifted and then the renal vessels (arterial+venous) of both sides are ligated through the rear peritoneum with a surgical needle. Then, the abdominal cavity is closed again. 0.3 ml (respectively 50 mmol/L) of the following contrast medium solution per animal is then administered intravenously: mixture of 1 part each of the compound of Example 1k), named compound 1 below, and the dysprosium complex of 10-(1-hydroxymethyl-2,3-dihydroxypropyl)-1,4,7-tris(carboxymethyl)-1,4,7,10-tetraazacyclododecane, produced analogously to the instructions in European Patent Application EP 448 191, named compound 2 below. Blood samples are taken with a catheter in the common carotid artery at the following times: 15, 30, 45, 60, 90 seconds, 3, 5, 10, 15 minutes p.i. In the blood samples obtained, the concentrations of gadolinium (Gd) and dysprosium (Dy) are measured with the aid of atomic emission spectrometry (ICP-AES) in each case in a parallel manner. The portion of the injected contrast medium of compound 1 (Gd) and compound 2 (Dy, comparison substance), remaining in the blood space, can be compared in the same animals by the different marking. Since a renal excretion is not possible, the decrease of the blood concentration can be attributed only to a distribution in the blood spaces and to the diffusion in the interstitial tissue.

Results: The diffusion of compound 1 in the interstitium is considerably slowed-down in comparison to an extracellular contrast medium compound 2 (see FIG. 1).

The extracellular contrast medium (compound 2) diffuses quickly into the interstitial spaces of the body, so that as early as after 3–5 minutes p.i., an equilibrium is reached (displayed by constant blood level). In contrast to this, not only are constantly higher blood concentrations measured with the cascade polymer (compound 1) (reference to smaller volume of distribution), in addition no equilibrium is reached over the entire examination period of 15 minutes (reference to diffusion into interstitial tissue proceeding only very slowly). This means that compound 1 behaves as a blood-pool contrast medium.

Example of an MR Angiography on Rabbits

The compound cited under Example 1k was studied on rabbits (CH. R. Kisslegg, ≈4 kg of body weight) in an MR angiography experiment (Ganzkörper [Whole-Body] MRT System Siemens Vision, 1.5 tesla, FISP 3D; TR: 400 ms; TE 15 ms; flip angle: 45°; coronal).

In a precontrast picture, only one to two major vessels are visible (e.g., abdominal aorta) in relatively poor contrast (signal intensity SI of these vessels against the background). After i.v. administration of 50 μmol of Gd/kg of body weight of the compound described in Example 1k, a marked increase in contrast (SI of the vessels/SI of the background) and a wide variety of minor blood vessels and capillaries (e.g., A. and V. femoralis, A. and V. mesenterica caudalis, A. and V. renalis, A. and V. subrenalis, etc.), which could not be detected before the administration of contrast medium, are visible.

Example of Lymph Node Accumulation in Guinea Pigs

The compound according to the invention that is cited under Example 1k was studied 30 minutes to 24 hours after subcutaneous administration (10 μmol of gadolinium/kg of body weight, hind paw s.c.) in stimulated guinea pigs (complete Freund's adjunct; in each case 0.1 ml i.m. in the right and left upper and lower legs; 2 weeks before administration of the test substances) to determine its lymph node accumulation in three successive lymph node stations (popliteal, inguinal, iliac). In this case, the results listed below (determination of gadolinium accumulation with the aid of ICP-AES) were obtained:

| Time of Lymph Node Removal | Gadolinium Accumulation in Three Successive Lymph Node Stations [μmol/1] [% of Dose/g of Tissue] | | | |
|---|---|---|---|---|
| | Popliteal | Inguinal | Iliac | Ratio |
| 30 min p. i | 921 μmol/1 20:1% | 387 μmol/1 8.5% | 215 μmol/1 4.7% | 10:4.2:2.3 |
| 90 min p. i. | 659 μmol/1 14.4% | 120 μmol/1 2.6% | 68 μmol/1 1.5% | 10:1.8:1.0 |
| 4 h p. i. | 176 μmol/1 3.9% | 79 μmol/1 1.7% | 47 μmol/1 1.0% | 10:4.5:2.7 |
| 24 h p. i. | 62 μmol/1 1.4% | 13 μmol/1 0.3% | 28 μmol/1 0.6% | 10:2.1:4.5 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A cascade polymer complex containing
   a) a complexing ligand of formula I $$A-\{X-[Y-(Z-<W-K_W>_Z)_4]_x\}_a \quad (I),$$

in which
   A stands for a nitrogen-containing cascade nucleus of base multiplicity a,
   X and Y independently of one another, stand for a direct bond or a cascade reproduction unit of reproduction multiplicity x or y,
   Z and W, independently of one another, stand for a cascade reproduction unit of reproduction multiplicity z or w,
   K stands for the radical of a complexing agent,
   a stands for a number from 2 to 12,
   x, y, z and w, independently of one another, stand for a number 1 to 4, and
   terminal amino groups are optionally acylated, provided that at least two reproduction units are different and that
   $16 \leq a \cdot x \cdot y \cdot z \cdot w \leq 64$,
   holds true for the product of the multiplicities,
   b) at least 16 ions of an element of atomic numbers 20 to 29, 39, 42, 44 or 57–83 and,
   c) optionally cations of inorganic and/or organic bases, amino acids or amino acid amides,
   wherein at least one of cascade reproduction units X, Y, Z and W, independently of one another, is selected from the group consisting of
   E,

E.

$$U^3-N\begin{matrix}U^1\\ \\U^2\end{matrix},$$

$$U^3-V\begin{matrix}\diagup U^1\\ N\diagdown U^2\\ \diagup U^4\\ \diagdown U^5\end{matrix}\begin{matrix} \\ \\ \diagup U^1\\ N\diagdown U^2\end{matrix},$$

and $$-CO-\underset{\underset{U^3-N\diagdown U^2}{\diagup U^1}}{\overset{\overset{U^3-N\diagdown U^2}{\diagup U^1}}{\bigcirc}}-L$$

in which
   $U^1$ stands for $Q^1$ or E,
   $U^2$ stands for $Q^2$ or E with
   E meaning the group $$-(CH_2)_o-CH_2-N\begin{matrix}\diagup Q^1\\ \diagdown Q^2\end{matrix},$$

in which
   o stands for a number from 1 to 6,
   $Q^1$ stands for a hydrogen atom or $Q^2$,
   $Q^2$ stands for a direct bond,
   $U^3$ stands for a $C_1$–$C_{20}$ alkylene chain which optionally is interrupted by 1 to 10 oxygen atoms, 1 to 2 —N(CO)$_q$—$R^2$ radicals, 1 to 2 phenylene radicals, 1 to 2 phenylenoxy radicals or combinations thereof, and optionally is substituted by 1 to 2 oxo, thioxo, carboxy, $C_1$–$C_5$ alkylcarboxy, $C_1$–$C_5$ alkoxy, hydroxy or $C_1$–$C_5$ alkyl groups, in which q stands for number 0 or 1 and $R^2$ stands for a hydrogen atom, a methyl or an ethyl radical, which optionally is substituted with 1–2 hydroxy or 1 carboxy group(s), L stands for a hydrogen atom or the group

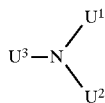

V stands for methine group

in which case $U^4$ means a direct bond or group M and $U^5$ has one of the meanings of $U^3$ or V stands for group

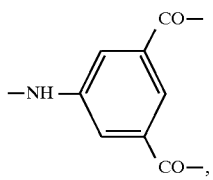

in which case $U^4$ and $U^5$ are identical and mean the direct bond or group M where M stands for a $C_{1-10}$-alkylene chain which optionally is interrupted by 1 to 3 oxygen atoms and optionally is substituted with 1 to 2 oxo groups, and wherein complexing agent radical K bound to the terminal nitrogen atoms of the last generation of reproduction unit W stand for a radical of general formula IA or IB

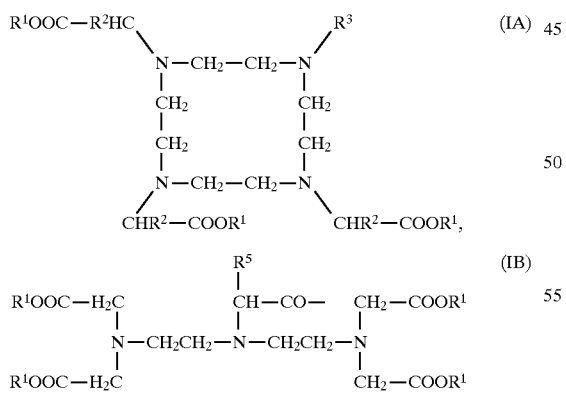

in which $R^1$ independently of one another, stand for a hydrogen atom or a metal ion equivalent of atomic numbers 20–29, 39, 42–44 or 57–83, $R^2$ stands for a hydrogen atom, a methyl or an ethyl radical which optionally is substituted with 1–2 hydroxy or 1 carboxy group(s), $R^3$ stands for a

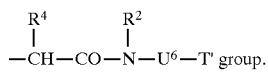

$R^4$ stands for a straight-chain, branched, saturated or unsaturated $C_1$–$C_{30}$ alkyl chain, which optionally is interrupted by 1–10 oxygen atoms, 1 phenylene group, 1 phenylenoxy group and optionally substituted by 1–5 hydroxy, 1–3 carboxy, 1-phenyl group(s), $R^5$ stands for a hydrogen atom or for $R^4$, $U^6$ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups, or 1–10 oxygen, 1–5 sulfur or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester, [and/or] 1–3 amino group(s) or combinations thereof, and the phenylene groups that are optionally contained can be substituted by 1–2 carboxy, 1–2 sulfo or 1–2 hydroxy groups, T stands for a —CO-α, —NHCO-α or —NHCS-α group, and α stands for the bonding site to the terminal nitrogen atoms of the last generation, of reproduction unit W.

2. A cascade polymer complex according to claim 1, wherein A means a nitrogen atom,

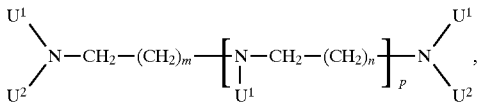

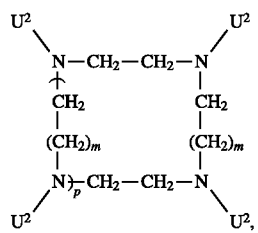

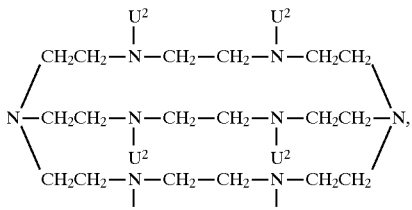

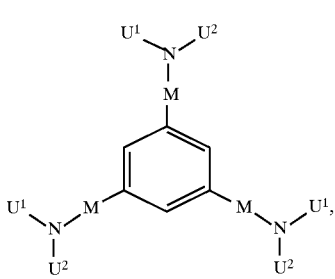

5,820,849

43

-continued

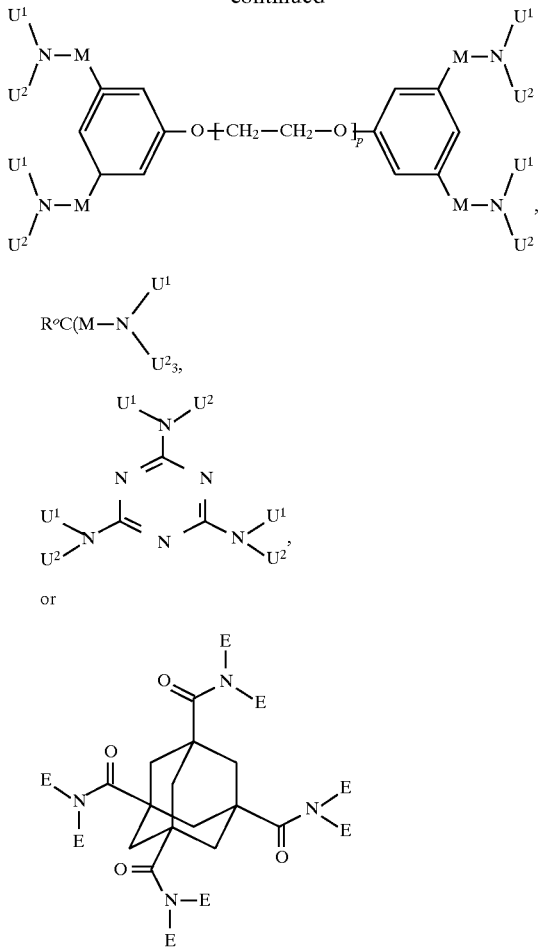

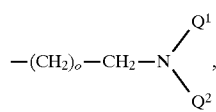

in which m and n independently stand for numbers 1 to 10, p stands for numbers 0 to 10, $U^1$ stands for $Q^1$ or E, $U^2$ stands for $Q^2$ or E with E meaning the group —(CH$_2$)$_o$—CH$_2$—N$\begin{smallmatrix}Q^1\\Q^2\end{smallmatrix}$, whereby o stands for numbers 1 to 6, $Q^1$ stands for a hydrogen atom or $Q^2$ and $Q^2$ stands for a direct bond, M stands for a $C_1$–$C_{10}$ alkylene chain which optionally is interrupted by 1 to 3 oxygen atoms and/or optionally is substituted with 1 to 2 oxo groups, $R^o$ stands for a branched or unbranched $C_1$–$C_{10}$ alkyl radical, a nitro, amino, carboxylic acid group or for

44

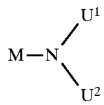

whereby the number of $Q^2$ elements equals the base multiplicity a.

3. A cascade polymer complex according to claim 1, wherein the $C_1$–$C_{20}$ alkylene chain that stands for $U^6$ contains the groups —CH$_2$—, —CH$_2$NHCO—, —NHCOCH$_2$O—, —NHCOCH$_2$OC$_6$H$_4$—, —N(CH$_2$CO$_2$H)—, —NHCOCH$_2$C$_6$H$_4$—, —NHCSNHC$_6$H$_4$—, —CH$_2$OC$_6$H$_4$—, or —CH$_2$CH$_2$O— and optionally is substituted by groups —COOH, or —CH$_2$COOH.

4. A cascade polymer complex according to claim 1, wherein $U^6$ stands for a

—CH$_2$—, —CH$_2$CH$_2$—, —CH$_2$CH$_2$CH$_2$—, —C$_6$H$_4$—, —C$_6$H$_{10}$—, —CH$_2$C$_6$H$_5$—,
—CH$_2$NHCOCH$_2$CH(CH$_2$CO$_2$H)—C$_6$H$_4$—,
—CH$_2$NHCOCH$_2$OCH$_2$—, or
—CH$_2$NHCOCH$_2$C$_6$H$_4$— group.

5. A cascade polymer complex according to claim 1, wherein radical $U^3$ contained in cascade reproduction units X, Y, Z and W stands for —CO—, —COCH$_2$OCH$_2$CO—, —COCH$_2$—, —CH$_2$CH$_2$—, —CONHC$_6$H$_4$—, —COCH$_2$CH$_2$CO—, —COCH$_2$—CH$_2$CH$_2$CO—, or —COCH$_2$CH$_2$CH$_2$CH$_2$CO—, radical $U^4$ stands for a direct bond, or for —CH$_2$CO—, radical $U^5$ stands for a direct bond, —(CH$_2$)$_4$—, —CH$_2$CO—, —CH(COOH)—, CH$_2$OCH$_2$CH$_2$—, —CH$_2$C$_6$H$_4$—, or CH$_2$—C$_6$H$_4$OCH$_2$CH$_2$—, radical E stands for a group

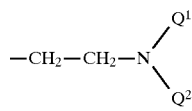

6. A cascade polymer complex according to claim 1, wherein cascade reproduction units X, Y, Z and W, independently of one another, stand for

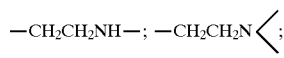

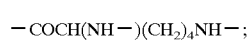

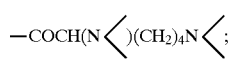

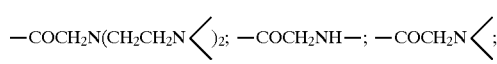

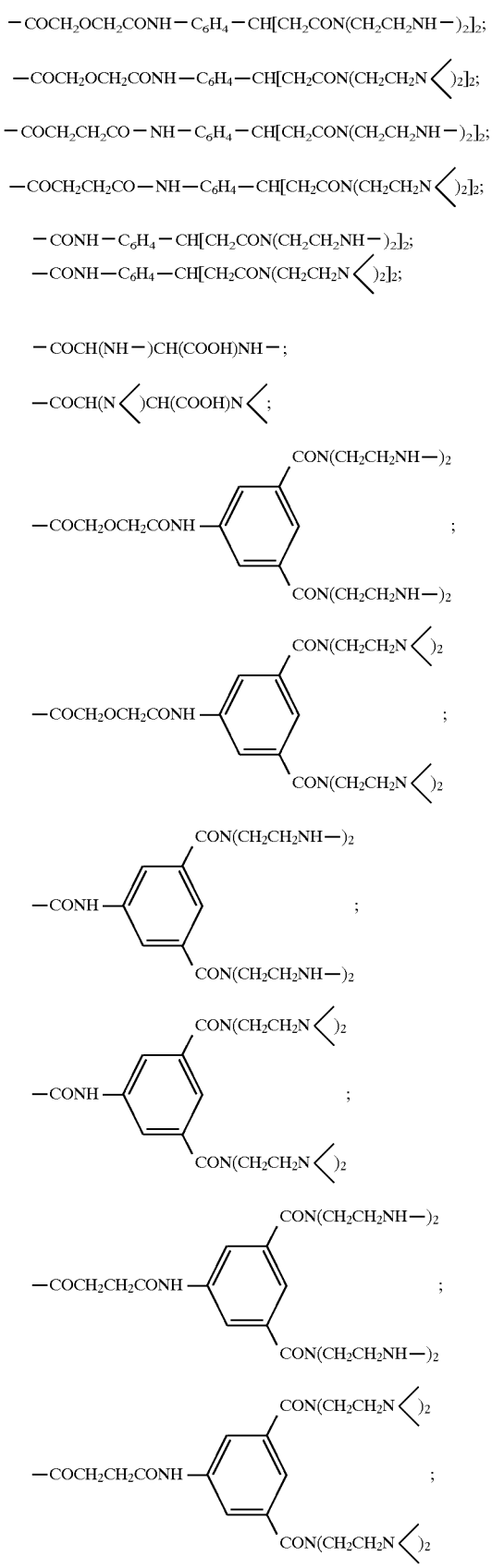

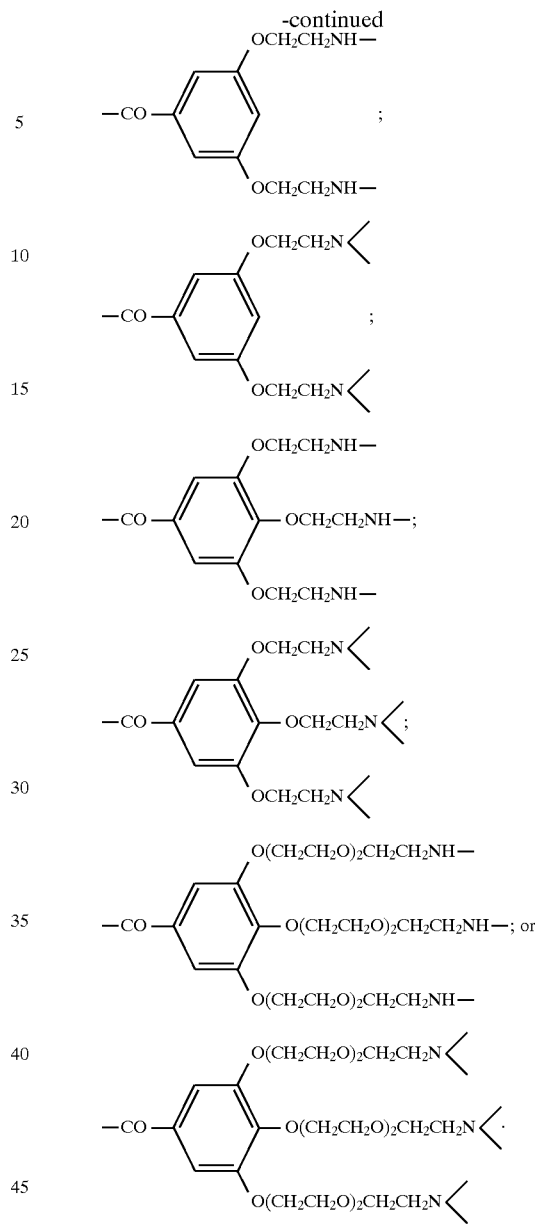

7. A cascade polymer complex according to claim 2, wherein m stands for a number from 1–3,
n stands for a number from 1–3,
o stands for 1,
p stands for a number from 0–3,
M stands for a —$CH_2$, —CO or —$CH_2$CO group and
$R^o$ stands for a —$CH_2NU^1U^2$, $CH_3$ or $NO_2$ group.

8. A pharmaceutical agent comprising at least one cascade polymer complex according to claim 1, and a pharmaceutically acceptable carrier.

9. A method of NMR diagnosis comprising administering at least one polymer complex according to claim 1.

10. A method for differentiating benign and malignant tumors in regions of the body without blood-brain barriers comprising imaging such tumors by administering a cascade polymer complex according to claim 1.

11. A process for the production of a cascade polymer complex according to claim 1, wherein a compound of general formula I'

A-{X-[Y-(Z-<W-β$_{W>2}$)$_y$]$_x$}a     (I'), in which p1 A stands for a nitrogen-containing cascade nucleus of base multiplicity a, X and Y, independently of one another, stand for a direct bond or a cascade reproduction unit of reproduction multiplicity x or y, Z and W, independently of one another, stand for a cascade reproduction unit of reproduction multiplicity z or w, a stands for numbers 2 to 12, x, y, z and w, independently of one another, stand for numbers 1 to 4 and β stands for the bonding site of the terminal NH groups of the last generation, of reproduction unit W, provided that at least two reproduction units are different and that for the product of the multiplicities, 16 ≦ a·x·y·z·w ≦ 64 holds true, is reacted with a complex of complexing agent K' of general formula I'A or I'B

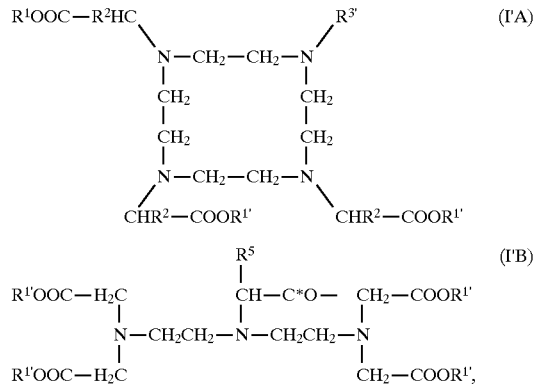

whereby

R$^{1'}$, independently of one another, stand for a hydrogen atom, a metal ion equivalent of atomic numbers 20–29, 39, 42–44, or 57–83 or an acid protective group, R$^2$ stands for a hydrogen atom, a methyl or an ethyl radical, which optionally is substituted with 1–2 hydroxy or 1 carboxy group(s), R$^{3'}$ stands for a

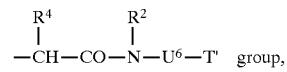

R$^4$ stands for a straight-chain, branched, saturated or unsaturated C$_1$–C$_{30}$ alkyl chain, which optionally is interrupted by 1–10 oxygen atoms, 1 phenylene group, 1 phenylenoxy group and optionally substituted by 1–5 hydroxy, 1–3 carboxy, 1-phenyl group(s), R$^5$ stands for a hydrogen atom or for R$^4$, U$^6$ stands for a straight-chain, branched, saturated or unsaturated C$_1$–C$_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur 1–5 nitrogen atom(s) or combinations thereof and optionally substituted by 1–5 hydroxy, 1–2 mercapto, 1–5 oxo, 1–5 thioxo, 1–3 carboxy, 1–5 carboxyalkyl, 1–5 ester, 1–3 amino group(s) or combinations thereof, whereby the phenylene groups that are optionally contained can be substituted by 1–2 carboxy, 1–2 sulfo or 1–2 hydroxy groups, T' stands for a —C*O, —COOH, —N=C=O or —N=C=S group, and C*O stands for an activated carboxyl group provided that—if K' stands for a complex—at least two, in the case of divalent metals, or three, in the case of trivalent metals, of substituents R$^1$ stand for a metal ion equivalent of the above-mentioned elements and that optionally other carboxyl groups are present in the form of their salts with inorganic bases, organic bases, amino acids or amino acid amides, clearing any optionally present protective groups, the thus obtained cascade polymers—if K' stands for a complexing agent—are reacted with at least one metal oxide or metal salt of an element of atomic numbers 20–29, 39, 42, 44, or 57–83 and optionally then in the cascade polymer complexes thus obtained, acid hydrogen atoms that are still present are completely or partially substituted by cations of inorganic and/or organic bases, amino acids, or amino acid amides and optionally still present free terminal amino groups are optionally acylated—before or after the metal complexing.

12. A process for the production of a pharmaceutical agent according to claim 8, wherein the cascade polymer complex, dissolved or suspended in water or physiological salt solution, optionally with the additives usual in galenicals, is brought into a form suitable for enteral or parenteral administration.

13. A cascade polymer complex according to claim 1, wherein a cascade reproduction unit X, Y, Z or W is E which is —CH$_2$—CH$_2$—N(Q$^1$Q$^2$).

14. A cascade polymer complex of claim 1, wherein at least one reproduction unit X, Y, Z or W is of the following formula:

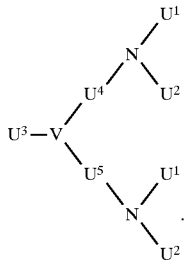

* * * * *